United States Patent
Umansky et al.

(10) Patent No.: US 8,648,017 B2
(45) Date of Patent: Feb. 11, 2014

(54) METHODS OF USING SMALL RNA FROM BODILY FLUIDS FOR DIAGNOSIS AND MONITORING OF NEURODEGENERATIVE DISEASES

(75) Inventors: Samuil R. Umansky, Princeton, NJ (US); Kira S. Sheinerman, New York, NY (US)

(73) Assignee: DiamiR, LLC, Princeton, NJ (US)

( * ) Notice: Subject to any disclaimer, the term of this patent is extended or adjusted under 35 U.S.C. 154(b) by 0 days.

(21) Appl. No.: 13/508,262

(22) PCT Filed: Nov. 4, 2010

(86) PCT No.: PCT/US2010/055495
§ 371 (c)(1),
(2), (4) Date: May 4, 2012

(87) PCT Pub. No.: WO2011/057003
PCT Pub. Date: May 12, 2011

(65) Prior Publication Data
US 2012/0252693 A1    Oct. 4, 2012

Related U.S. Application Data

(60) Provisional application No. 61/258,185, filed on Nov. 4, 2009.

(51) Int. Cl.
*C12Q 1/68*      (2006.01)
*C40B 40/06*    (2006.01)
*C40B 30/04*    (2006.01)

(52) U.S. Cl.
USPC ............................ 506/9; 435/6.11; 506/16

(58) Field of Classification Search
USPC .............................. 506/9, 16; 435/6.1
See application file for complete search history.

(56) References Cited

U.S. PATENT DOCUMENTS

| | | |
|---|---|---|
| 2007/0161004 A1 | 7/2007 | Brown et al. |
| 2008/0171667 A1 | 7/2008 | Brown et al. |
| 2009/0075258 A1* | 3/2009 | Latham et al. ............... 435/6 |
| 2009/0081640 A1* | 3/2009 | Umansky et al. ............. 435/5 |
| 2009/0176723 A1 | 7/2009 | Brown et al. |
| 2010/0151480 A1 | 6/2010 | Taylor et al. |
| 2010/0167937 A1 | 7/2010 | Goldknopf et al. |
| 2010/0167948 A1 | 7/2010 | Krichevsky et al. |
| 2010/0184046 A1 | 7/2010 | Klass et al. |
| 2010/0216139 A1* | 8/2010 | Galas et al. ................. 435/6 |
| 2010/0227908 A1 | 9/2010 | Cairns et al. |
| 2010/0267804 A1 | 10/2010 | Port et al. |
| 2010/0279292 A1 | 11/2010 | Marsh et al. |
| 2010/0286044 A1 | 11/2010 | Litman et al. |
| 2010/0323357 A1 | 12/2010 | Nana-Sinkam et al. |
| 2011/0111976 A1 | 5/2011 | Fare et al. |
| 2011/0160285 A1 | 6/2011 | Anderson et al. |
| 2011/0160290 A1 | 6/2011 | Tewari et al. |

FOREIGN PATENT DOCUMENTS

| | | |
|---|---|---|
| WO | WO2005118806 | 12/2005 |
| WO | WO2007073737 | 7/2007 |
| WO | WO2008153692 | 12/2008 |
| WO | WO2008153692 A2 | 12/2008 |
| WO | WO 2008153692 A2 * | 12/2008 |
| WO | WO2009009457 | 1/2009 |
| WO | WO2009009457 A1 | 1/2009 |
| WO | WO2009012468 | 1/2009 |
| WO | WO2009015357 | 1/2009 |
| WO | WO2009025852 | 2/2009 |
| WO | WO2009025852 A2 | 2/2009 |
| WO | WO2009036236 | 3/2009 |
| WO | WO2009070653 | 6/2009 |
| WO | WO2009114681 | 9/2009 |
| WO | WO2009132273 | 10/2009 |
| WO | WO2009143379 | 11/2009 |
| WO | WO2010054386 | 5/2010 |

OTHER PUBLICATIONS

Yoo et al., Oxidative Stress Regulated Genes in Nigral Dopaminergic Neuronal Cells: Correlation with the Known Pathology in Parkinson's Disease, Molecular Brain Research, 2003, 110, 76-84.*
Braak, et al., Neuropathological staging of Alzheimer's related changes, Acta Neuropathol., vol. 82, pp. 239-259, 1991.
Geekiyanage, et al., Blood serum miRNA: Non-invasive biomarkers for Alzheimer's disease, Exp Neurol., vol. 235, pp. 491-496, 2012, ePub Dec. 1, 2011.
Hebert, et al., Loss of microRNA cluster miR-29a/b-1 in sporadic Alzheimer's disease correlates with increased BACE1/beta-secretase expression, Proc Natl Acad Sci USA, vol. 105, pp. 6415-6420, 2008.
International Search Report and Written Opinion of the International Searching Authority for International Application No. PCT/US12/34098, mailed Jul. 17, 2012.
International Search Report and Written Opinion of the International Searching Authority for International Application No. PCT/US12/34025, mailed Sep. 28, 2012.

(Continued)

*Primary Examiner* — Maria Leavitt
*Assistant Examiner* — Amy M Bunker
(74) *Attorney, Agent, or Firm* — Troutman Sanders LLP

(57) ABSTRACT

Described are methods for detection of neuronal pathologies using quantitative analysis in bodily fluids of synapse and/or neurite small RNAs and application of these methods to early diagnosis and monitoring of neurodegenerative diseases and other neurological disorders.

12 Claims, 9 Drawing Sheets

(56) References Cited

OTHER PUBLICATIONS

Kemppainen, et al., MicroRNAs as biomarkers in blood and other biofluids, poster 2010? [Retrieved from the Internet Sep. 8, 2012: <http://www.asuragen.com/pdfs/posters/biomarkers.pdf>].
McDonald, et al., Analysis of circulating microRNA: preanalytical and analytical challenges, Clin Chem., vol. 57, pp. 833-840, 2011.
Satoh, Molecular network of microRNA targets in Alzheimer's disease brains, Exp Neurol., vol. 235, pp. 436-446, 2012, ePub Sep. 16, 2011.
Schipper, et al., MicroRNA expression in Alzheimer blood mononuclear cells, Gene Regul. Syst. Bio., Vo., 1, pp. 263-274, 2007.
Sempere et al., "Expression profiling of mammalian microRNAs uncovers a subset of brain-expressed microRNAs with possible roles in murine and human neuronal differentiation", Genome Biology (online), Biomed Central Ltd, GB, 2004, vol. 5, No. 3, pp. R13.1-R13.11.
Schratt et al., "A brain-specific microRNA regulartes dendritic spine development", Nature (London)., 2006, vol. 439, No. 7074, pp. 283-289.
Lugli et al., "Expression of microRNAs and their precursors in synaptic fractions of adult mouse forebrain", Journal of Neurochemistry, 2008, vol. 106., No. 2, pp. 650-661.
Lugli et al., "File S2. Entire list of measured human, rat and mouse microRNAs by microarray after filtering and normalization", Journal of Neurochemistry, 2008, vol. 106, No. 2, p. 7PP.
Maes et al., "MicroRNA: Implications for Alzheimer Disease and other Human CNS Disorders", Current Genomics, 2009, vol. 10, No. 3, pp. 154-168.
Maes et al., "Methodology for discovery of Alzheimer's disease blood-based biomarkers", Journals of Gerontology—Series A Biological Sciences and Medical Sciences, 2009, vol. 64, No. 6, pp. 636-645.
Wang et al., "The expression of microRNA miR-107 decreases early in Alzheimer's disease and may accelerate disease progression through regulation of beta-site amyloid precursor protein-cleaving enzyme 1", Journal of Neuroscience, 2008, vol. 28, No. 5, pp. 1213-1223.
International Search Report mailed Jun. 6, 2011, which issued in corresponding International Application No. PCT/US2010/0055495.
Adachi, Taichi, et al., Plasma MicroRNA 499 as a Biomarker of Acute Myocardial Infarction, Clinical Chemistry, vol. 56, No. 7, pp. 1183-1185, 2010.
Albert MS, et al., The diagnosis of mild cognitive impairment due to Alzheimer's disease: Recommendations from National Institute on Aging—Alzheimer's Association workgroups on diagnostic guidelines for Alzheimer's disease, Alzheimers Dement, vol. 7, pp. 270-279, 2011.
Backes, Christina, et al., A dictionary on microRNAs and their putative target pathways, Nucleic Acids Res, vol. 38, pp. 4476-4486, 2010.
Bak, Mads, et al., MicroRNA expression in the adult mouse central nervous system, RNA., vol. 14(3), pp. 432-444, 2008.
Bartel DP, MicroRNAs: target recognition and regulatory functions, Cell, vol. 136, pp. 215-233, 2009.
Bishop DL, et al., Axon branch removal at developing synapses by axosome shedding, Neuron, vol. 44, pp. 651-661, 2004.
Brase, Jan C. et al., Circulating miRNAs are correlated with tumor progression in prostate cancer, International Journal of Cancer, vol. 128(3), pp. 608-616, 2011.
Brase, Jan C., et al., Serum microRNAs as non-invasive biomarkers for cancer, Molecular Cancer, vol. 9, pp. 306-315, 2010.
Charras, Guillaume T., et al., Life and times of a cellular bleb, Biophys J., vol. 94(5), pp. 1836-1853, 2008.
Chen, Xi, Characterization of microRNAs in serum: a novel class of biomarkers for diagnosis of cancer and other diseases, Cell Research, vol. 18, pp. 997-1006, 2008.
Chim, Stephen S.C., et al., Detection and Characterization of Placental MicroRNAs in Maternal Plasma, Clinical Chemistry, vol. 54(3), pp. 482-490, 2008.
Eaton BA, et al., Synapse disassembly, Genes Dev., vol. 17, pp. 2075-2082, 2003.
Edbauer, D., et al., Regulation of synaptic structure and function by FMRP-associated microRNAs miR-125b and miR-132, Neuron, vol. 65(3), pp. 373-384, 2010.
Emery, VO., Alzheimer disease: are we intervening too late? J Neural Transm., vol. 118(9), pp. 1361-1378, 2011.
Fackler OT, Grosse R., Cell motility through plasma membrane blebbing, J Cell Biol., vol. 181(6), pp. 879-884, 2008.
Griffiths-Jones S., et al., miRBase: microRNA sequences, targets and gene nomenclature, Nucleic Acids Res., vol. 34, Database issue: D140-D144, 2006.
Hua Y-J., et al., Identification and target prediction of miRNAs specifically expressed in rat neural tissue, BMC Genomics, vol. 10, pp. 214-225, 2009.
Hunter, Melissa Piper, et al., Detection of microRNA Expression in Human Peripheral Blood Microvesicles, PLoS ONE, 3(11): e3694, 2008.
Ji, Xi, et al., Plasma miR-208 as a Biomarker of Myocardial Injury, Clinical Chemistry, vol. 55(11), pp. 1944-1949, 2009.
Koirala S, et al., Pruning an Axon Piece by Piece, Neuron, vol. 44, pp. 578-580, 2004.
Kosaka, Nobuyoshi, et al., Secretory Mechanisms and Intercellular Transfer of MicroRNAs in Living Cells, J Biol Chem., vol. 285(23), pp. 17442-17452, 2010.
Kye MJ, et al., Somatodendritic microRNAs identified by laser capture and multiplex RT-PCR, RNA, vol. 13, pp. 1224-1234, 2007.
Landgraf, Pablo, A Mammalian microRNA Expression Atlas Based on Small RNA Library Sequencing, Cell, vol. 129(7), pp. 1401-1414, 2007.
Lee EJ, et al., Systematic evaluation of microRNA processing patterns in tissues, cell lines, and tumors, RNA, vol. 14, pp. 35-42, 2008.
Liang Y, et al., Characterization of microRNA expression profiles in normal human tissues, BMC Genomics, vol. 8, pp. 166-185, 2007.
Liu, Da-Zhi, et al., Brain and blood microRNA expression profiling of ischemic stroke, intracerebral hemorrhage, and kainate seizures, J Cereb Blood Flow Metab., advance online publication, 2009, doi:10.1038/jcbfm.2009.186, pp. 1-12.
Lodes, Michael J., et al., Detection of Cancer with Serum miRNAs on an Oligonucleotide Microarray. PLoS ONE, vol. 4(7): e6229, 2009.
Low LK, et al., Axon pruning: an essential step underlying the developmental plasticity of neuronal connections, Phil Trans R Soc B., vol. 361, pp. 1531-1544, 2006.
McKhann GM, et al., The diagnosis of dementia due to Alzheimer's disease: Recommendations from National Institute on Aging—Alzheimer's Association workgroups on diagnostic guidelines for Alzheimer's disease, Alzheimers Dement., vol. 7, pp. 263-269, 2011.
Miller G, Alzheimer's biomarker initiative hits its stride, Science, vol. 326, pp. 386-389, 2009.
Mitchell PS, et al., Circulating microRNAs as stable blood-based markers for cancer detection, Proc Natl Acad Sci USA, vol. 105, pp. 10513-10518, 2008.
Mitchell, Patrick S., et al., Circulating microRNAs as stable blood-based markers for cancer detection, Proc Natl Acad Sci USA, vol. 105(30): 10513-10518, 2008.
Natera-Naranjo, Orlangie, et al., Identification and quantitative analyses of microRNAs located in the distal axons of sympathetic neurons, RNA, vol. 16, pp. 1516-1529, 2010.
Olsen, Line, et al., MicroRNAs Show Mutually Exclusive Expression Patterns in the Brain of Adult Male Rats. PLoS ONE, vol. 4(10): e7225, 2009.
Peltier HJ, et al., Normalization of microRNA expression levels in quantitative RT-PCR assays: identification of suitable reference RNA targets in normal and cancerous human solid tissues, RNA, vol. 14, pp. 844-852, 2008.
Ray S, et al., Classification and prediction of clinical Alzheimer's diagnosis based on plasma signaling proteins, Nat Med., vol. 13, pp. 1359-1362, 2007.
Satoh J-i, MicroRNAs and Their Therapeutic Potential for Human Diseases: Aberrant MicroRNA Expression in Alzheimer's Disease Brain, J Pharmacol Sci., vol. 114, pp. 269-275, 2010.

(56) References Cited

OTHER PUBLICATIONS

Schmand B, et al., Value of Neurophysiological Tests, Neuroimaging, and Biomarkers for Diagnosing Alzheimer's Disease in Younger and Older Age Cohorts, J Am Geriatr Soc., vol. 59, pp. 1705-1710, 2001.

Schratt, Gerhard, microRNAs at the synapse, Nature Reviews Neuroscience, vol. 10, pp. 842-849, 2009.

Skog J, et al., Glioblastoma microvesicles transport RNA and proteins that promote tumour growth and provide diagnostic biomarkers, Nat Cell Biol., vol. 10(12), pp. 1470-1476, 2008.

Sperling RA, et al., The diagnosis of dementia due to Alzheimer's disease: Recommendations from National Institute on Aging-Alzheimer's Association workgroups on diagnostic guidelines for Alzheimer's disease, Alzheimers Dement., vol. 7, pp. 280-292, 2011.

Wang, Guo-Kun, et al., Circulating microRNA: a novel potential biomarker for early diagnosis of acute myocardial infarction in humans, European Heart Journal, vol. 31, Issue 6, pp. 659-666, 2010.

Wang, Kai, et al., Circulating microRNAs, potential biomarkers for drug-induced liver injury, Proc Natl Acad Sci USA, vol. 106(11), pp. 4402-4407, 2009.

Yoshiyama Y, et al., Synapse Loss and Microglial Activation Precede Tangles in P301S Tauopathy Mouse Model, Neuron., vol. 53, pp. 337-351, 2007.

Cogswell, John P., et al., "Identification of miRNA Changes in Alzheimer's Disease Brain and CSF Yields Putative Biomarkers and Insights into Disease Pathways", Journal of Alzheimer's Disease , vol. 14, pp. 27-41, 2008.

Kosaka, Nobuyoshi, et al., "Circulating microRNA in body fluid: a new potential biomarker for cancer diagnosis and prognosis", Cancer Sci., vol. 101, pp. 2087-2092, 2010.

Laterza, Omar F., et al., "Plasma MicroRNAs as Diagnostically Sensitive and Specific Biomarkers of Tissue Injury", Clinical Chemistry, vol. 55:11, pp. 1-7, 2009.

Lugli, Giovanni, et al., "Expression of microRNAs and their precursors in synaptic fractions of adult mouse forebrain", Journal of Neurochemistry, vol. 106, pp. 650-661, 2008.

Lugli, Giovanni, et al., "File S2. Entire list of measured human, rat and mouse microRNAs by microarray after filtering and normalization," Journal of Neurochemistry, vol. 106, 2008.

Maes, Olivier C., et al. "Methodology for Discovery of Alzheimer's Disease Blood-Based Biomarkers", J Gerontol A Biol Sci Med Sci, vol. 64A, pp. 636-645, 2009.

Maes, Olivier C., et al. MicroRNA: Implications for Alzheimer Disease and other Human CNS Disorders, Current Genomics, vol. 10, pp. 154-168, 2009.

Schratt, Gerhard M., et al., "A brain-specific microRNA regulates dendritic spine development", Nature, vol. 439, pp. 283-289, 2006.

Sempere, Lorenzo F, et al., "Expression profiling of mammalian microRNAs uncovers a subset of brain-expressed microRNAs with possible roles in murine and human neuronal differentiation", Genome Biology, vol. 5:R13, pp. R13.1-R13.11, 2004.

Wang, Wang-Xia, et al., "The Expression of MicroRNA miR-107 Decreases Early in Alzheimer's Disease and May Accelerate Disease Progression through Regulation of β-Site Amyloid Precursor Protein-Cleaving Enzyme 1", The Journal of Neuroscience, vol. 28, pp. 1213-1223, 2008.

International Search Report for International Appl. No. PCT/US2010/055495, mailed Jun. 6, 2011.

International Preliminary Report on Patentability for International Appl. No. PCT/US2010/055495, dated May 8, 2012.

\* cited by examiner

METHODS OF USING SMALL RNA FROM BODILY FLUIDS FOR DIAGNOSIS AND MONITORING OF NEURODEGENERATIVE DISEASES

CROSS REFERENCE TO PRIOR APPLICATIONS

This is a U.S. National Phase application under 35 U.S.C. §371 of International Patent Application No. PCT/US2010/055495, filed Nov. 4, 2010, and claims the priority of U.S. Provisional Patent Application No. 61/258,185, filed Nov. 4, 2009, both of which are incorporated by reference herein in their entirety. The International Application published in English on May 12, 2011 as WO 2011/057003 under PCT Article 21(2).

TECHNICAL FIELD OF THE INVENTION

The present invention is directed to methods for noninvasive or minimally invasive detection of pathological changes in brain or other neurons by quantifying neurite and/or synapse small RNA, particularly miRNA, in bodily fluids and application of these methods to early diagnosis and monitoring of neurodegenerative diseases and other neurological disorders.

BACKGROUND OF THE INVENTION

Neurodegenerative diseases comprise a large group of pathologies caused by metabolic changes in brain cells, loss of synapses and other compartments of neurons, and finally neuronal death. For review see *Neurodegenerative diseases: From Molecular Concepts to Therapeutic Targets*. Editors: R. von Bernhardi, N.C. Inestrosa, Nova Publishers, 2008. This group of diseases includes Mild Cognitive Impairment (MCI), Alzheimer's disease (AD), Lewy Body dementia, Parkinson's disease (PD), Huntington's disease (HD), frontotemporal dementia (FTD), vascular dementia, HIV Associated Neurocognitive Disorders (HAND), multiple sclerosis (MS), amyotrophic lateral sclerosis (ALS), prion diseases, different ataxias, and others. Due to increased lifespan, neurodegenerative diseases have become very common in developed countries. There are about 6 million people living with AD in the US only, 70-80 million people are in the risk group and $148 billion is spent in the US for AD patient treatment and care. Drug development and successful treatment of AD and other neurodegenerative diseases are significantly complicated by the absence of effective methods for their early diagnosis and monitoring. Development of effective diagnostic methods is further complicated by the strong brain potential to compensate for the dysfunction and loss of neurons over a long period of time. This results in late clinical manifestation of disease symptoms when treatment cannot be very successful due to serious morphologic changes in the brain including the massive loss of neurons. Thus, diagnostic methods based on detection of early events in the disease development are particularly desirable.

Neurodegenerative diseases are characterized by neuronal death in different disease-specific areas of the brain. However, the neuronal loss is a relatively late event, typically following synaptic dysfunction, synaptic loss, neurite retraction, and the appearance of other abnormalities such as axonal transport defects. See, e.g., Bredesen, Molecular Neurodegeneration 2009, 4:27; Siskova et al., Am J. Pathol. 2009, 175(4):1610-21; Kielar et al., Hum Mol Genet. 2009, 18(21): 4066-4080; Nimmrich and Ebert, Rev Neurosci. 2009, 20:1-12; Bellizzi et al., J Neuroimmune Pharmacol. 2006, 1:20-31; Milnerwood and Raymond, J. Physiol. 2007, 585:817-831; Waataja et al., J. Neurochem. 2008, 104:364-375; Fuhrmann et al., J. Neurosci. 2007, 27:6224-6233; Yoshiyama et al., Neuron. 2007, 53:337-351; Wishart et al., J Neuropathol Exp Neurol. 2006, 65:733-739; Gylys et al., Neurochem Int. 2004; 44:125-131; Conforti et al., Trends Neurosci. 2007, 30:159-166; Baloyannis et al., J Neurol Sci. 2006, 248:35-41; Diaz-Hernandez et al., FASEB J. 2009, 23:1893-1906; Spampanato et al., Neuroscience 2008, 157:606-620; Wade et al., Brain Res. 2008, 1188:61-68; Centonze et al., J. Neurosci. 2009, 29:3442-3452; Wegner et al., Neurology. 2006, 67:960-967; Dupuis and Loeffler, Curr Opin Pharmacol. 2009, 9:341-346; Revuelta, et al. Am J Alzheimers Dis Other Demen 2008 23: 97-102. Numerous studies are devoted to description of axon destruction with shedding of membrane-enclosed "axosomes", axon, dendrite and spine pruning, and disassembly of synapses (Goda, Davis, Neuron 2003, 40:243-264; Eaton, Davis, Genes Development, 2003, 17:2075-2082; Koiral, Ko, Neuron, 2004, 44:578-580; Bishop et al., Neuron, 2004, 44:651-661; Low, Cheng, Phil. Trans. R. Soc. B 2006 361, 1531-1544).

Currently, diagnosis of AD and other forms of dementia is based on analysis of the patient's cognitive function. As mentioned above, due to effective compensatory mechanisms in the brain, the decrease of cognitive function is usually registered when a disease is in its later stages and fewer treatments are available. New imaging techniques, which are becoming increasingly popular (e.g., positron emission tomography (PET), computed tomography (CT), magnetic resonance imaging (MRI), multiphoton imaging, magnetoencephalography (MEG), electroencephalography (EEG) etc.), are helpful, however, they are currently not sufficiently sensitive and specific for detecting early stages of a disease before major morphological changes occur (Mucke, Nature, 2009, 461: 895-897; Mistur et al., J. Clin. Neurol., 2009, 5:153-166; Miller, Science, 2009, 326:386-389; Perrin et al., Nature, 2009, 461: 916-922).

The existing diagnostic molecular tests for AD and other forms of dementia can be divided into two groups. The first group is based on analysis of single nucleotide polymorphisms (SNP), which is helpful for predicting a higher risk of a disease but not for diagnostics (Bettens et al.; Hum Mol Genet. 2010, 19(R1):R4-R11). The second group uses analysis of proteins involved in AD pathogenesis or brain-specific proteins, like neural thread protein (NTP), in bodily fluids (Schipper, Alzheimer's & Dementia. 2007, 3:325-332). However, these tests are not sufficiently sensitive and specific. Recently published data have demonstrated high sensitivity of AD detection by measuring concentrations of three protein biomarkers (beta-amyloid protein 1-42, total tau protein, and phosphorylated tau181P protein) in the cerebrospinal fluid (CSF) (Meyer et al., Arch Neurol. 2010, 67:949-956). The high invasiveness of the CST collection procedure makes such tests impractical and challenging for everyday clinical use.

Metabolic changes occurring in neurodegenerative diseases cause the destruction of spines, dendrites, axons, and synapse loss, and the latter, most likely, induces neuronal death (Bredesen, Molecular Neurodegeneration 2009, 4:27). Similar processes happen during embryonic brain development. Numerous neurons are trying to establish intercellular contacts, those neurons that do it successfully survive, and other neurons die (Butts et al., Cell Death Differ. 2008, 15:1178-1186; Enokido and Hatanaka, Gan To Kagaku Ryoho. 1994, 21:615-620; Gasic and Nicotera, Toxicol Lett. 2003, 139:221-227).

Axon destruction with shedding of membrane-enclosed "axosomes", axon, dendrite and spine pruning, and disassembly of synapses lead to appearance of cell-free vesicles containing cytoplasmic components of neurons, axons, neurites, spines and synapses, including proteins, RNA and their degradation products. There are other processes leading to liberation of these compounds into the extracellular medium, in particular, blebbing (Charras et al., Biophys. J. 2008, 94:1836-1853; Fackler, Grosse, J. Cell Biol. 2008, 181:879-884), exocytosis (Skog et al. Nat Cell Biol., 2008, 10:1470-1476) and other forms of active secretion.

MicroRNAs (miRNAs) are a class of non-coding RNAs whose final product is an approximately 22 nt functional RNA molecule. They play important roles in the regulation of target genes by binding to complementary regions of messenger transcripts to repress their translation or regulate degradation (Griffiths-Jones Nucleic Acids Research, 2006, 34, Database issue: D140-D144). Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (e.g., Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). There are other classes of less characterized small RNAs (reviewed in Kim, Mol. Cells, 2005, 19: 1-15).

Many of miRNAs are specific to or over-expressed in certain organs/tissues/cells. See, e.g., Hua et al., BMC Genomics 2009, 10:214; Liang et al., BMC Genomics. 2007, 8:166; Landgraf et al., Cell. 2007, 129:1401-1414; Lee et al., RNA. 2008, 14:35-42.

Some miRNAs, including those that are cell-specific, are enriched in certain cellular compartments, particularly in axons, dendrites and synapses. See, e.g., Schratt et al., Nature. 439:283-289, 2006; Lugli et al., J. Neurochem. 106:650-661, 2008; Bicker and Schratt, J Cell Mol Med., 12:1466-1476, 2008; Smalheiser and Lugli, Neuromolecular Med. 11:133-140, 2009; Rajasethupathy, Neuron. 63:714-716, 2009; Kye, RNA 13:1224-1234, 2007; Yu et al., Exp Cell Res. 314:2618-2633, 2008; Cougot, et al., J. Neurosci. 28:13793-13804, 2008; Kawahara, Brain Nerve. 60:1437-1444, 2008; Schratt G. Rev Neurosci. 2009; 10:842-849.

Expression and concentrations of miRNAs are regulated by various physiological and pathological signals. Changes in expression of some miRNAs were found in neurons of Alzheimer's and other neurodegenerative disease patients. Hébert and De Strooper, Trends Neurosci. 32:199-206, 2009; Saba et al., PLoS One. 2008; 3:e3652; Kocerha et al., Neuromolecular Med. 2009; 11:162-172; Sethi and Lukiw, Neurosci Lett. 2009, 459:100-104; Zeng, Mol Pharmacol. 75:259-264, 2009; Cogswell et al., Journal of Alzheimer's Disease. 14:27-41, 2008; Schaefer et al., J. Exp. Med. 204:1553-1558, 2007; Hébert, Proc Natl Acad Sci USA. 2008; 105:6415-6420; Wang et al., J. Neurosci. 2008, 28:1213-1223; Nelson et al., Brain Pathol. 2008; 18:130-138; Lukiw, Neuroreport. 2007; 18:297-300.

Due to their small size, miRNAs can cross the blood-brain, placental and kidney barriers. Analysis of cell/tissue-specific miRNAs in bodily fluids was proposed for detection of in vivo cell death (U.S. Patent Pub. No 20090081640; Laterza et al., Clin Chem. 2009, 55:1977-1983).

Cognitive function testing and brain imaging, which are currently used as main methods for diagnosis of neurodegenerative diseases such as AD, allow only detection of later stages of disease and are not sufficiently specific. There is still a great need in the art to develop methods for early diagnosis of neurodegenerative diseases and other neurological disorders in mammals prior to occurrence of major morphological changes and massive neuronal cell death.

SUMMARY OF THE INVENTION

The present invention addresses these and other needs by providing a novel highly sensitive and noninvasive or minimally invasive diagnostic and monitoring methods based on quantification in bodily fluids of synapse and/or neurite small RNAs. The methods of the present invention allow diagnosis and monitoring of neurodegenerative diseases and other neurological disorders prior to occurrence of major morphological changes and massive neuronal cell death and thus have numerous clinical implications. For example, the use of the methods of the present invention can lead to enhanced effectiveness of currently available treatments for neurodegenerative diseases and other neurological disorders as such treatments could be administered at a significantly earlier stage of the disease. The use of the methods of the present invention can also allow development of new effective therapeutic and/or preventive treatments and can decrease costs and increase efficiency of clinical trials associated with such development.

In the first object, the present invention provides a method for diagnosing a neuronal pathology in a subject, which comprises:

a. determining the level of at least one synapse and/or neurite small RNA in a bodily fluid sample from the subject;

b. comparing the level of the small RNA in the bodily fluid sample from the subject with a control level of the small RNA, and c. (i) identifying the subject as being afflicted with the neuronal pathology when the level of the small RNA in the bodily fluid sample from the subject is increased as compared to the control or (ii) identifying the subject as not being afflicted with the neuronal pathology when the level of the small RNA in the bodily fluid sample from the subject is not increased as compared to the control.

In another aspect, the invention provides a method for diagnosing a neuronal pathology in a subject, which comprises:

a. determining the level of a synapse and/or neurite small RNA in a bodily fluid sample from the subject;

b. determining the level of a neuronal body small RNA (e.g., miR-181a or miR-491-5p) in a bodily fluid sample from the subject;

c. determining the ratio of the levels of the small RNAs determined in steps (a) and (b);

d. comparing the ratio of the levels of the small RNAs determined in step (c) with a corresponding control ratio, and e. (i) identifying the subject as being afflicted with the neuronal pathology when the ratio of the levels of the small RNAs determined in step (c) is higher than the corresponding control ratio or (ii) identifying the subject as not being afflicted with the neuronal pathology when ratio of the levels of the small RNAs determined in step (c) is not higher than the corresponding control ratio.

In a related aspect, the invention provides a method for diagnosing Alzheimer's disease (AD) in a subject, which comprises:

a. determining the level of at least one synapse or neurite small RNA in a bodily fluid sample from the subject;

b. comparing the level of the small RNA in the bodily fluid sample from the subject with a control level of the small RNA, and c. (i) identifying the subject as being afflicted with AD when the level of the small RNA in the bodily fluid sample from the subject is increased as compared to the control or (ii) identifying the subject as not being afflicted with AD when the level of the small RNA in the bodily fluid sample from the subject is not increased as compared to the control.

In another related aspect, the invention provides a method for diagnosing mild cognitive impairment (MCI) in a subject, which comprises:

a. determining the level of at least one synapse or neurite small RNA in a bodily fluid sample from the subject;

b. comparing the level of the small RNA in the bodily fluid sample from the subject with a control level of the small RNA, and c. (i) identifying the subject as being afflicted with MCI when the level of the small RNA in the bodily fluid sample from the subject is increased as compared to the control or (ii) identifying the subject as not being afflicted with MCI when the level of the small RNA in the bodily fluid sample from the subject is not increased as compared to the control.

In any of the above diagnostic methods, the control level of the small RNA can be, for example, (i) the level of said small RNA in a similarly processed bodily fluid sample from an age-matched control subject, (ii) the level of said small RNA in a similarly processed bodily fluid sample from the same subject obtained in the past, or (iii) a predetermined standard.

Any of the above diagnostic methods can further comprise normalizing the level of the small RNA in the bodily fluid sample from the subject and in the control to the level of a small RNA which is not expressed in brain (e.g., miR-10b or miR-141).

In another aspect, the invention provides a method for monitoring development of a neuronal pathology in a subject, which comprises:

a. determining the level of at least one synapse or neurite small RNA in two or more bodily fluid samples from the subject, wherein the samples have been obtained at spaced apart time points (e.g., within 1-48 months intervals), and b. comparing the levels of the small RNA between the earlier obtained and later obtained bodily fluid sample(s).

Such method can further comprise (c) (i) determining that the development of the neuronal pathology in the subject is accelerated if the level of the small RNA is increased in the later obtained bodily fluid sample(s) as compared to the earlier obtained sample(s); (ii) determining that the neuronal pathology in the subject continues to develop at the same rate if the level of the small RNA is not changed in the later obtained bodily fluid sample(s) as compared to the earlier obtained sample(s), and (iii) determining that the development of the neuronal pathology in the subject is slowed down if the level of the small RNA is decreased in the later obtained bodily fluid sample(s) as compared to the earlier obtained sample(s).

In an additional aspect, the invention provides a method for monitoring the effectiveness of a treatment of a neuronal pathology in a subject, which comprises:

a. determining the level of at least one synapse or neurite small RNA in a bodily fluid sample from the subject obtained prior to initiation of the treatment;

b. determining the level of the small RNA in one or more bodily fluid sample(s) from the subject obtained in the course of or following the treatment (e.g., within 1 week-12 months intervals), and c. comparing the level of the small RNA determined in steps (a) and (b), and optionally between different samples in step (b).

Such method can further comprise (d) (i) determining that the treatment is effective if the level of the small RNA has decreased in the course of or following the treatment or (ii) determining that the treatment is not effective if the level of the small RNA has not decreased in the course of or following the treatment.

Non-limiting examples of neuronal pathologies which can be diagnosed and monitored using any of the above methods include neurodegenerative diseases (such as, e.g., Alzheimer's disease (AD), Parkinson's disease (PD), Lewy Body dementia, Huntington's disease (HD), frontotemporal dementia (FTD), vascular dementia, HIV Associated Neurocognitive Disorders (HAND), mild cognitive impairment (MCI), mixed dementia, Creutzfeldt-Jakob Disease (CJD), normal pressure hydrocephalus, Wernicke-Korsakoff syndrome, multiple sclerosis (MS), amyotrophic lateral sclerosis (ALS), prion diseases, and different ataxias) and neuronal pathologies associated with an encephalopathy or neuropathy.

In any of the above methods, a neuronal pathology can be diagnosed and monitored prior to massive neuronal cell death characteristic of said pathology.

In one embodiment, the small RNA used in any of the methods of the invention is present in synapses. In another embodiment, the small RNA used in any of the methods of the invention is present in spines. In yet another embodiment, the small RNA used in any of the methods of the invention is present in axons. In a further embodiment, the small RNA used in any of the methods of the invention is present in dendrites.

In one embodiment, the small RNA used in any of the methods of the invention is miRNA. Non-limiting examples of synapse and/or neurite miRNAs useful in any of the methods of the invention include miR-7, miR-9, miR-9*, miR-25, miR-26a, miR-26b, miR-98, miR-124, miR-125b, miR-128, miR-132, miR-134, miR-138, miR-146, miR-182, miR-183, miR-200b, miR-200c, miR-213, miR-292-5p, miR-297, miR-322, miR-323-3p, miR-325, miR-337, miR-339, miR-345, miR-350, miR-351, miR-370, miR-425, miR-429, miR-433-5p, miR-446, miR-467, and miR-874. In one specific embodiment, the miRNA is selected from the group consisting of miR-7, miR-125b, miR-128, miR-132, miR-323-3p, miR-370, and miR-874.

In one embodiment, any of the methods of the invention comprise determining the level of two or more synapse and/or neurite small RNAs.

Non-limiting examples of bodily fluid samples useful in any of the methods of the invention include blood plasma, serum, urine, and saliva.

Non-limiting examples of methods for determining the level of small RNAs useful in any of the methods of the invention include hybridization, RT-PCR, and sequencing.

In one embodiment, prior to step (a) in any of the above methods, the small RNA is purified from the bodily fluid sample.

Any of the above methods can further comprise the step of reducing or eliminating degradation of the small RNA.

DETAILED DESCRIPTION OF THE INVENTION

Figure 1A:
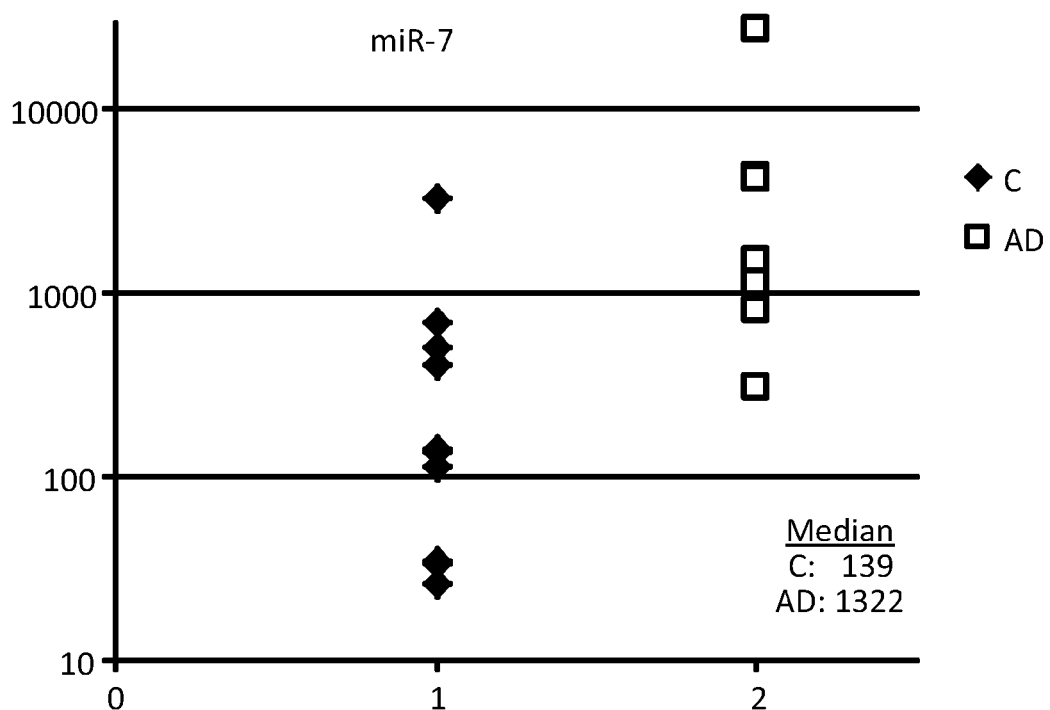
FIGS. 1A-G are graphs showing comparisons of miRNA concentrations in plasma of AD patients and age-matched controls. All concentrations were normalized per ubiquitous miR-16 and presented in relative units (ordinate axis). miR-7 (A), miR-125b (B), miR-128 (C), miR-132 (D), and miR-323-3p (E) are neurite and/or synapse miRNA; miR-181a (F) and miR-491-5p (G) are neuronal body miRNA.
Figure 1B:
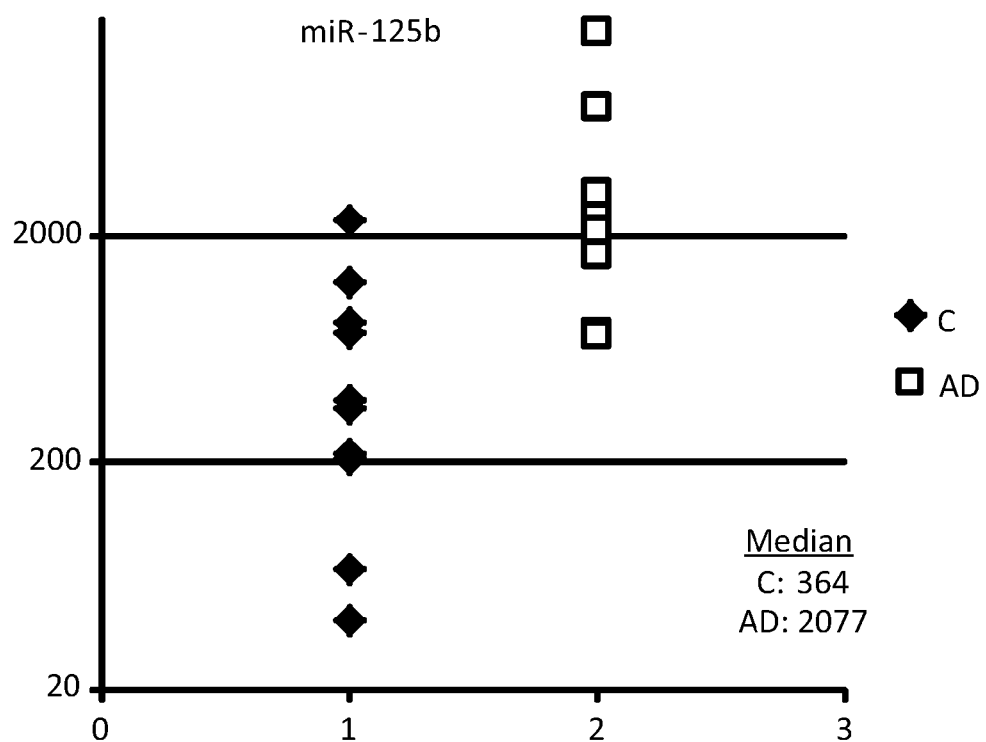
Figure 1C:
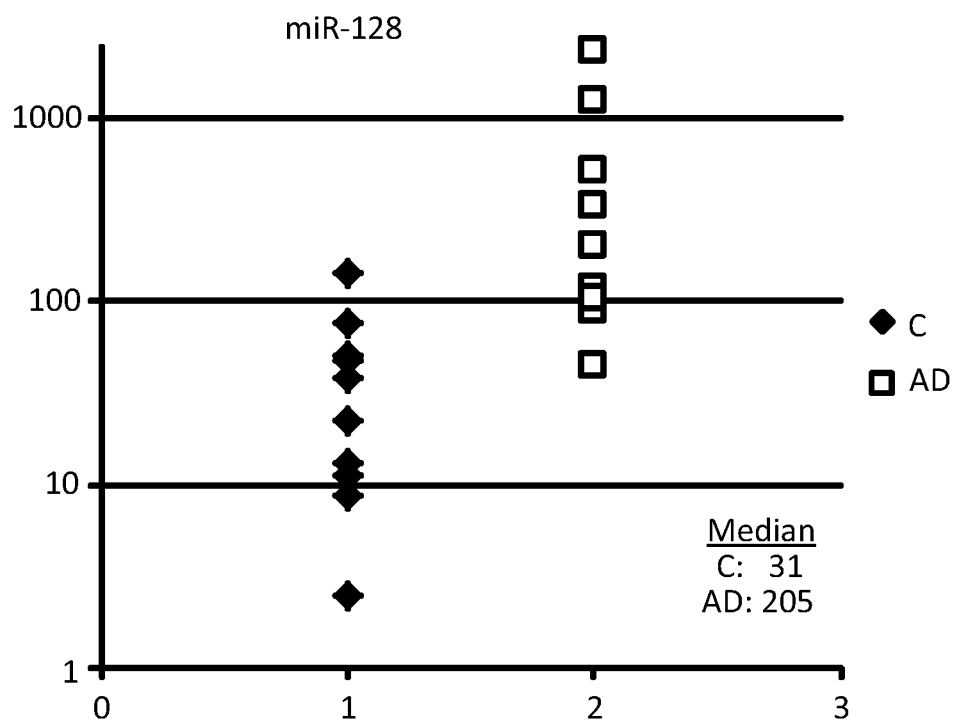
Figure 1D:
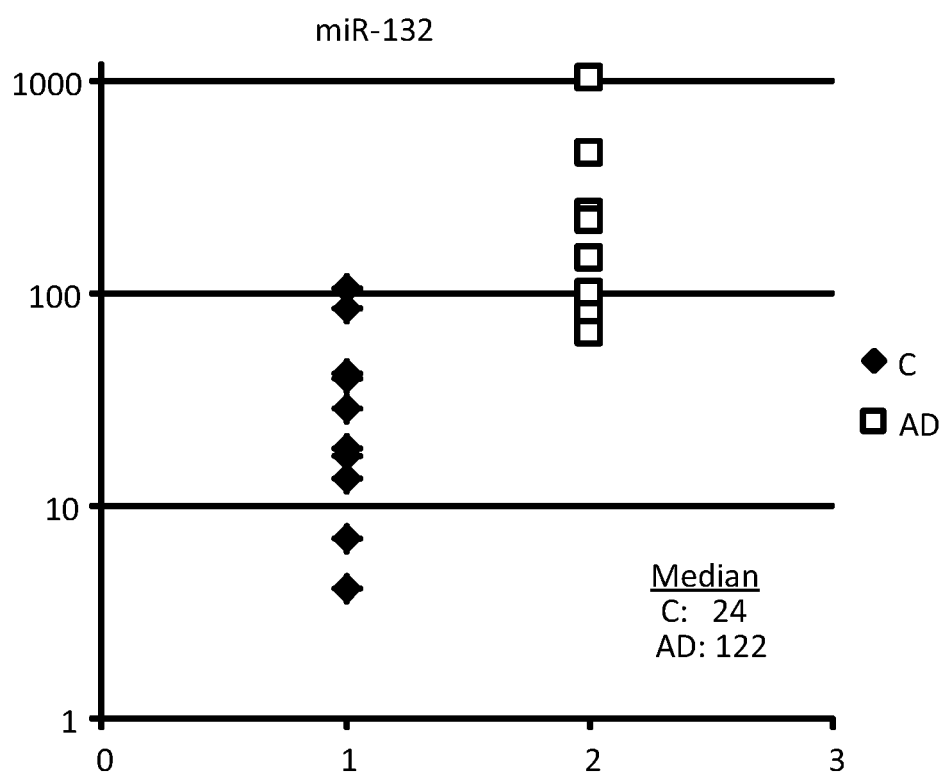
Figure 1E:
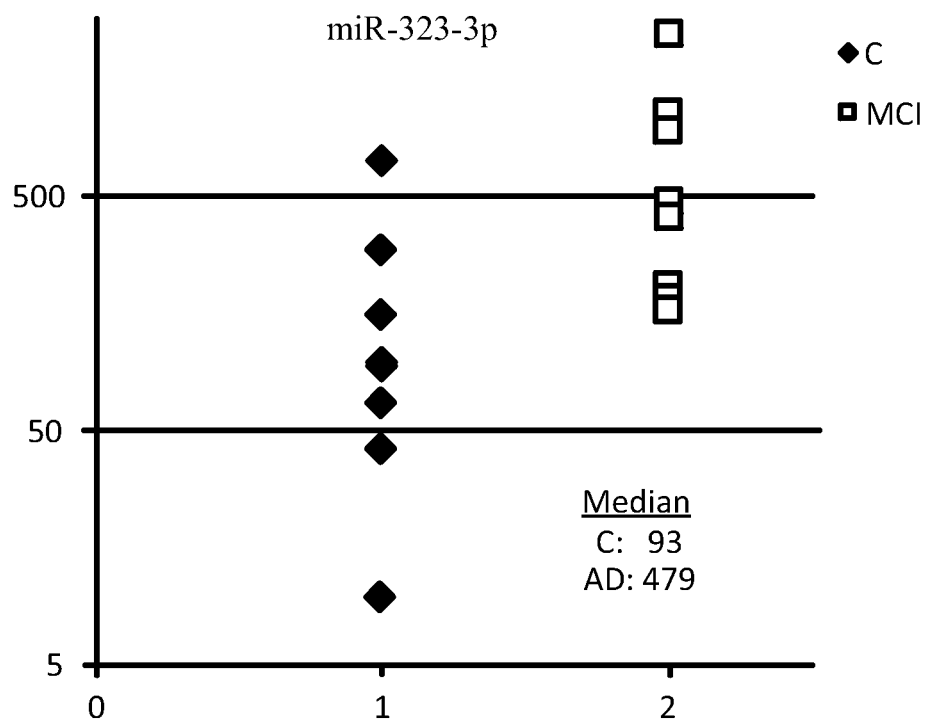
Figure 1F:
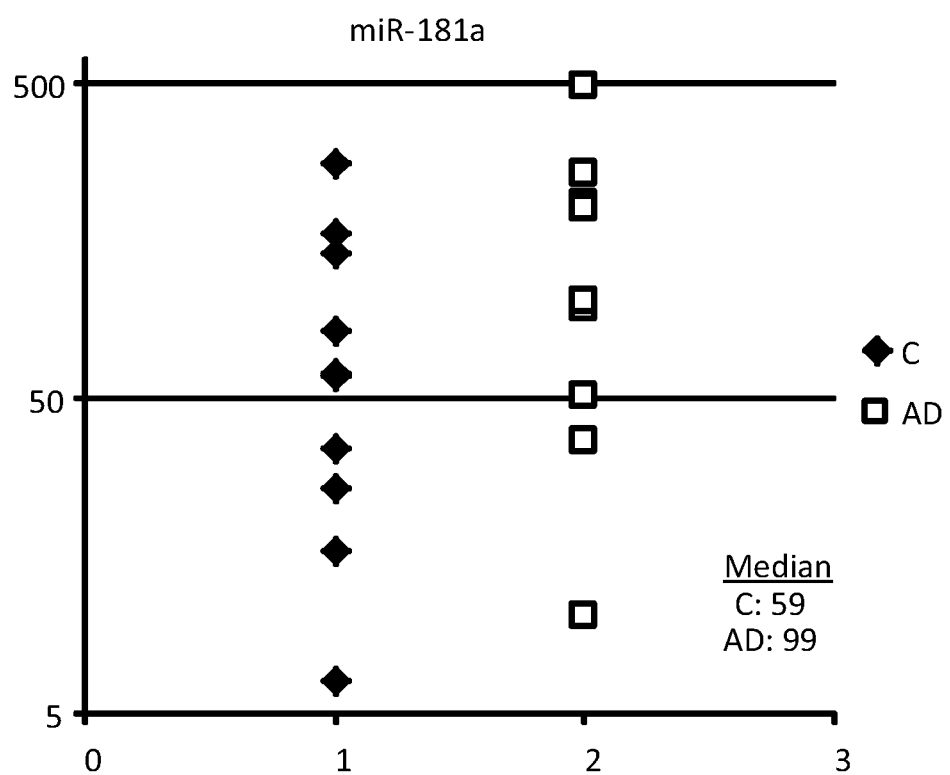
Figure 1G:
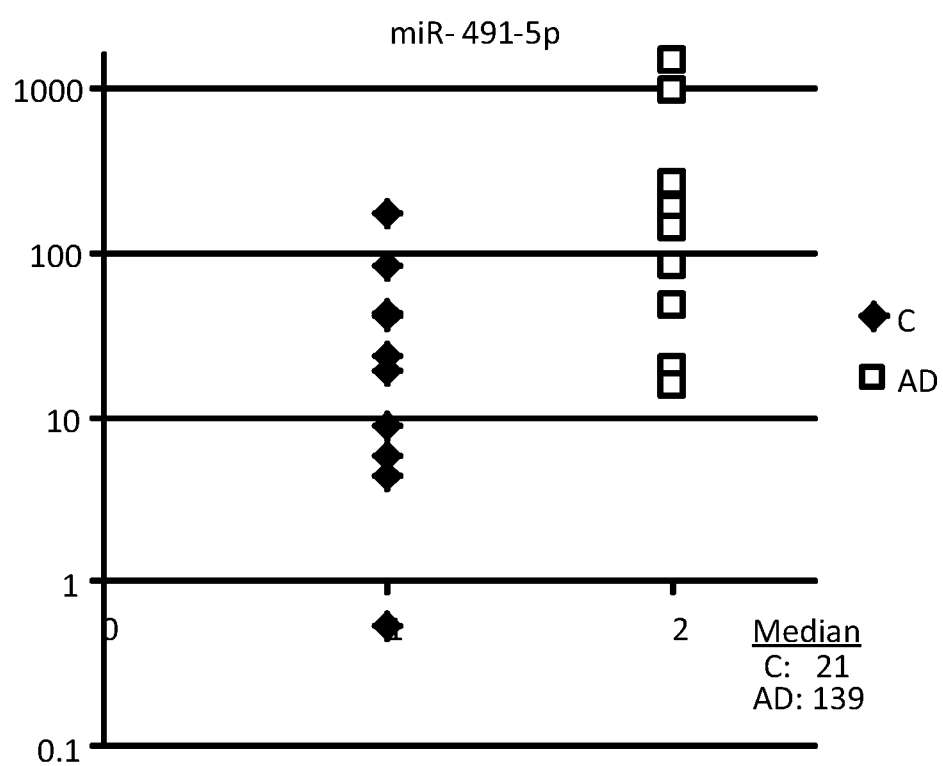
Figure 2A:
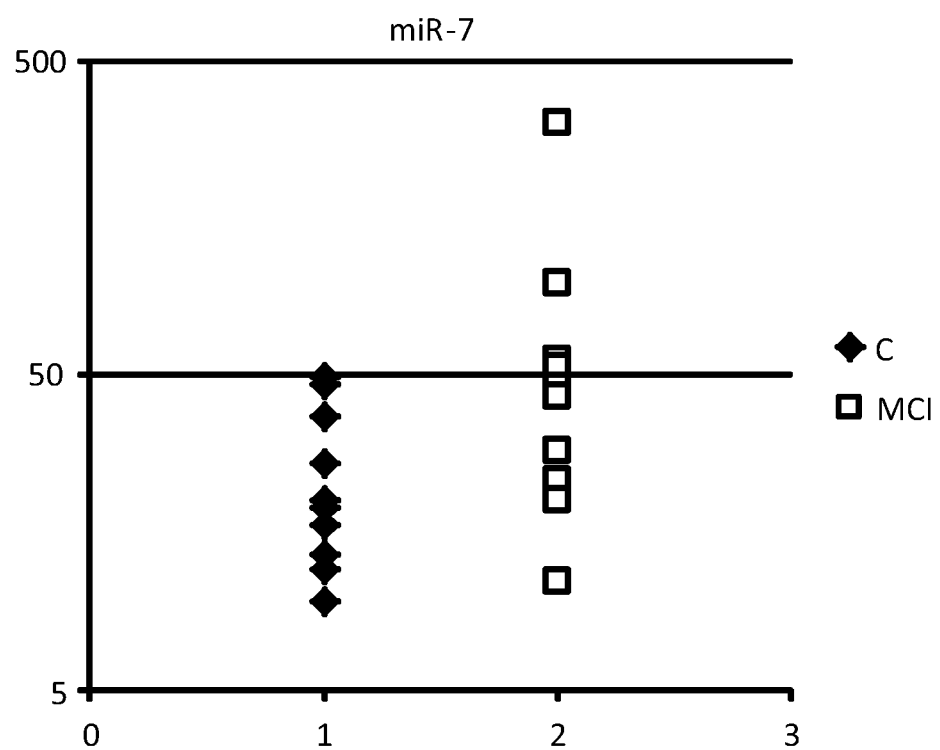
FIGS. 2A-D are graphs showing comparison of miRNA concentrations in plasma of MCI patients and age-matched controls. All concentrations were normalized per spiked miRNA and presented in relative units (ordinate axis). miR-7 (A) and miR-874 (B) are neurite and/or synapse miRNA; miR-181a (C) and miR-491-5p (D) are neuronal body miRNA.
Figure 2B:
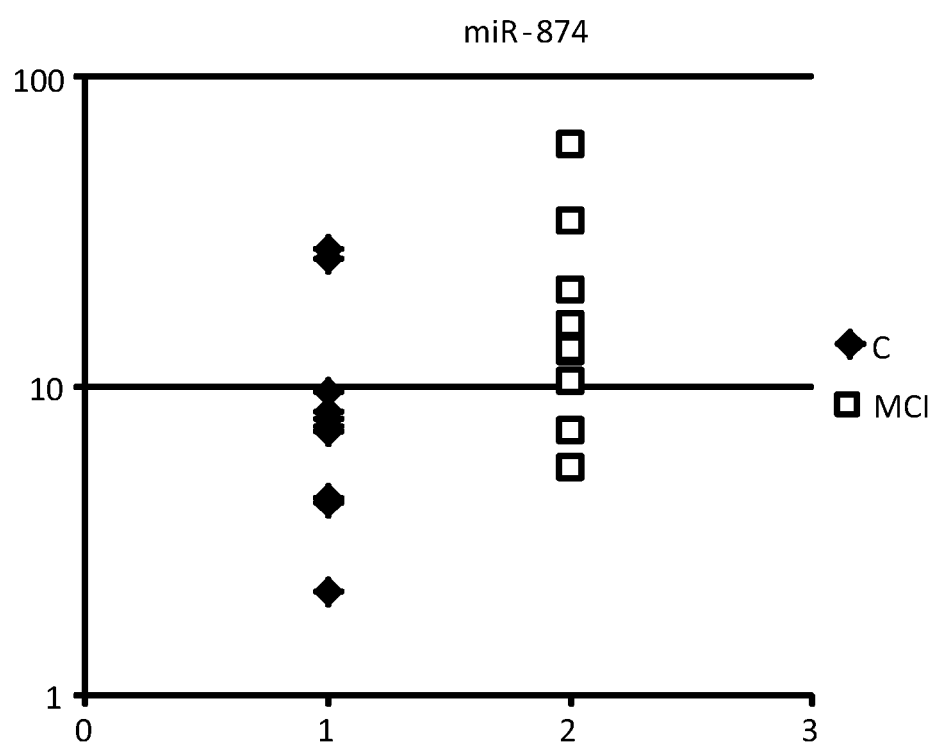
Figure 2C:
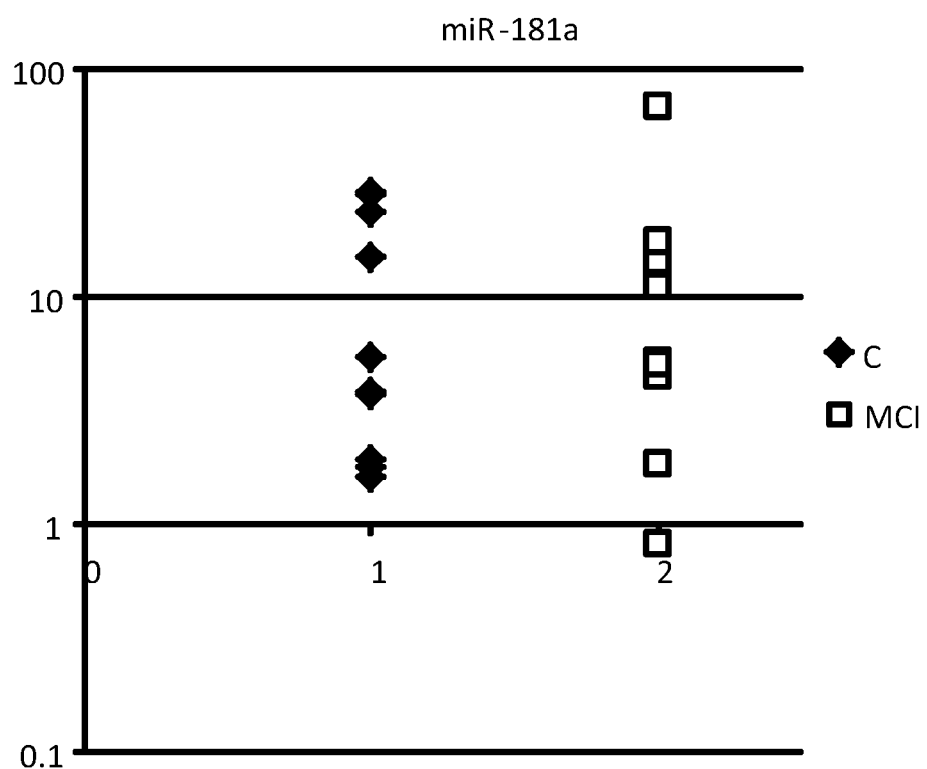
Figure 2D:
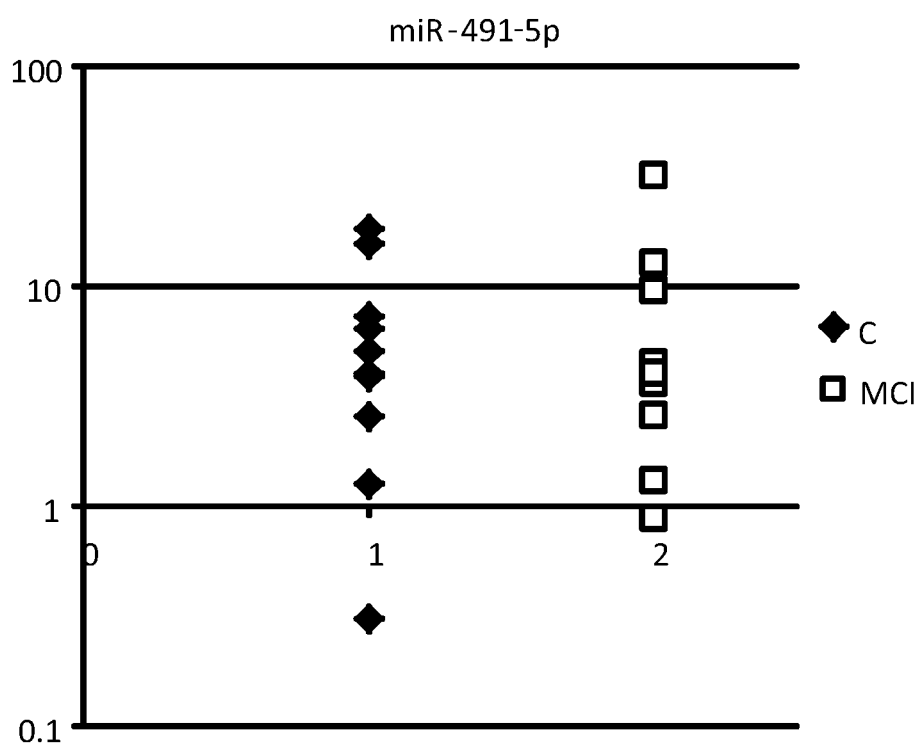

The present invention is based on the inventors' realization that since neurite (axon and/or dendrite and/or spine) destruction and synapse loss as well as some metabolic events precede neuronal death in the course of development of neurodegenerative diseases, methods based on detection of those phenomena could be used for earlier disease diagnosis than the ones based on detecting cell death.

The instant invention is further based on the inventors' discovery that levels of synapse and/or neurite miRNAs increase in bodily fluids of patients with Mild Cognitive Impairment (MCI) and/or Alzheimer's disease (AD) compared to respective age-matched controls reflecting excessive destruction of neurites and/or loss of synapses.

Within the meaning of the present invention, the term "synapse and/or neurite small RNA" refers to small RNA (e.g., miRNA or BC200 RNA) which (i) is "neuron-enriched", i.e., is present in increased amounts (e.g., at least 5-times higher concentrations) in neurons, as compared to cell types that can be a source of significant amounts of small RNA in a bodily fluid being tested and (ii) is present in a synapse and/or neurite (i.e., axon and/or dendrite and/or spine). To be useful in the diagnostic methods of the present invention, such synapse and/or neurite small RNA should be detectable in bodily fluids as a result of its release from neurons (e.g., due to neurite/synapse destruction or neuronal death).

The present invention provides a novel highly sensitive and noninvasive or minimally invasive method for diagnosing a neuronal pathology (e.g., a neuronal pathology associated with a neurodegenerative disease or another neurological disorder) in a subject, said method comprising determining the level in a bodily fluid sample from the subject (e.g., blood plasma or serum, urine, saliva, or other bodily fluids) of one or more synapse and/or neurite small RNA (e.g., miRNA or BC200 RNA). Specifically, this method comprises (a) determining the level of at least one synapse and/or neurite small RNA in a bodily fluid sample from the subject; (b) comparing the level of the small RNA in the bodily fluid sample with a control level of the small RNA (e.g., a similarly processed bodily fluid sample from a control subject [e.g., an age-matched control or the same subject in the past (e.g., 1, 3, 6, 12, 24, 36, or 48 months earlier)] or a predetermined standard), and (c) (i) identifying the subject as being afflicted with the neuronal pathology when the level of the small RNA in the bodily fluid sample from the subject is increased as compared to the control or (ii) identifying the subject as not being afflicted with the neuronal pathology when the level of the small RNA in the bodily fluid sample from the subject is not increased as compared to the control.

The diagnostic method of the invention makes possible early diagnosis of neurodegenerative diseases and other neurological disorders, e.g., prior to occurrence of major morphological changes and/or massive neuronal cell death associated with such diseases and disorders.

Furthermore, analysis of synapse and/or neurite small RNAs significantly enhances the sensitivity of the small RNA detection as compared to detecting neuronal body small RNAs which are not present or depleted in synapses and neurites, because the amount of synapses and neurites in the brain is $10^3$ times higher than the amount of neurons. This approach also provides detailed and comprehensive information for monitoring disease development and treatment effectiveness, since various specific events in neurons (e.g., changes in miRNA profile, their secretion, neurite degradation, synapse loss, and finally neuronal death) can be detected and quantitated.

Differences in levels of synapse and/or neurite small RNAs in bodily fluids of subjects having neurodegenerative diseases or other neurological disorders as compared to normal subjects detectable by the method of the present invention may be due to (i) disease-associated destruction of neurites and/or synapses, (ii) disease-associated changes in expression or metabolism of these small RNAs, (iii) disease-associated changes in transport and intracellular distribution of these small RNAs, (iv) disease-associated changes in secretion of these small RNAs (Rabinowits et al. Clin Lung Cancer, 2009, 10:42-46), as well as other causes.

In a separate embodiment, the invention provides a related diagnostic method for diagnosing a neuronal pathology which comprises (a) determining the level of a synapse and/or neurite small RNA in a bodily fluid sample from the subject; (b) determining the level of a neuronal body small RNA in a bodily fluid sample from the subject; (c) determining the ratio of the levels of the small RNAs determined in steps (a) and (b); (d) comparing the ratio of the levels of the small RNAs determined in step (c) with a corresponding control ratio, and (e) (i) identifying the subject as being afflicted with the neuronal pathology when the ratio of the levels of the small RNAs determined in step (c) is higher than the corresponding control ratio or (ii) identifying the subject as not being afflicted with the neuronal pathology when ratio of the levels of the small RNAs determined in step (c) is not higher than the corresponding control ratio.

Within the meaning of the present invention, the term "neuronal body small RNA" refers to small RNA (e.g., miRNA) which (i) is "neuron-enriched", i.e., is present in increased amounts (e.g., at least 5-times higher concentrations) in neurons, as compared to cell types that can be a source of significant amounts of small RNA in a bodily fluid being tested and (ii) is absent from or present in significantly lower concentrations in neurites or synapses than in neuronal cell bodies.

In another related embodiment, the present invention provides a method for monitoring development of a neuronal pathology (e.g., a neuronal pathology associated with a neurodegenerative disease or another neurological disorder) by periodically (e.g., every 1, 3, 6, 12, 24, 36, 48 months) obtaining samples of a bodily fluid from a subject under observation and determining changes in the level of one or more synapse and/or neurite small RNA (e.g., miRNA or BC200 RNA) in the bodily fluid. Specifically, this method comprises (a) determining the level of at least one synapse and/or neurite small RNA in two or more bodily fluid samples from the subject, wherein the samples have been obtained at spaced apart time points, and (b) comparing the levels of the small RNA between the earlier obtained and later obtained bodily fluid sample(s). If the level of the small RNA is increased in the later obtained bodily fluid sample(s) as compared to the earlier obtained sample(s), this is indicative of acceleration of development of the neuronal pathology in the subject. If the level of the small RNA is not changed in the later obtained bodily fluid sample(s) as compared to the earlier obtained sample(s), this is indicative that the neuronal pathology in the subject continues to develop at the same rate. If the level of the small RNA is decreased in the later obtained bodily fluid sample(s) as compared to the earlier obtained sample(s), this is indicative of slow down in development of the neuronal pathology in the subject.

In another related embodiment, the invention provides a method for monitoring the effectiveness of a treatment of a neuronal pathology (e.g., a neuronal pathology associated with a neurodegenerative disease or another neurological disorder) in a subject by determining changes in the level of one or more synapse and/or neurite small RNA in bodily fluid samples from the subject, wherein said samples have been obtained prior to initiation of the treatment and at different time points (e.g., every 1 week, 2 weeks, 1 month, 3 months, 6 months, 12 months, 24 months, 36 months, 48 months) in the course of or following the treatment. Specifically, this method comprises (a) determining the level of at least one synapse and/or neurite small RNA in a bodily fluid sample from the subject obtained prior to initiation of the treatment; (b) determining the level of the small RNA in one or more bodily fluid sample(s) from the subject obtained in the course of or following the treatment, and (c) comparing the level of the small RNA determined in steps (a) and (b), and optionally between different samples in step (b). If the level of the small RNA has decreased in the course of or following the treatment, this is indicative that the treatment is effective. If the level of the small RNA has not decreased in the course of or following the treatment, this is indicative that the treatment is not effective. This method can also involve comparison with placebo treated patients or other relevant controls.

The diagnostic and monitoring methods of the invention are useful for detecting and monitoring any stage of development of a neuronal pathology (e.g., a neuronal pathology associated with a neurodegenerative disease or another neurological disorder) and provide the advantage of a simple and minimally invasive (or noninvasive) assay. As noted above, unlike methods known in the art, the methods of the invention allow for diagnosis and monitoring of neuronal pathologies prior to occurrence of major morphological changes and/or massive neuronal cell death associated with such pathologies.

The methods of the present invention can be used to diagnose and monitor various neuronal pathologies including, without limitation, neurodegenerative diseases (e.g., Alzheimer's disease (AD), Parkinson's disease (PD), Lewy Body dementia, Huntington's disease (HD), frontotemporal dementia (FTD), vascular dementia, HIV Associated Neurocognitive Disorders (HAND), mild cognitive impairment (MCI), mixed dementia, Creutzfeldt-Jakob Disease (CJD), normal pressure hydrocephalus, Wernicke-Korsakoff syndrome, multiple sclerosis (MS), amyotrophic lateral sclerosis (ALS), prion diseases, different ataxias, etc.), various encephalopaties (e.g, viral encephalopaties such as AIDS dementia) and neuropathies (e.g., glaucoma [optical neuropathy], spinal muscular atrophy, etc.). In a separate embodiment of the present invention, a spectrum of various small RNAs (e.g., various miRNAs) can be analyzed for differential diagnosis of various neurodegenerative diseases with similar clinical symptoms, for example, different forms of dementia.

Neurite and/or synapse small RNAs useful in the methods of the present invention include, without limitation, miRNAs such as miR-7; miR-9; miR-9*; miR-25; miR-26a; miR-26b; miR-98; miR-124; miR-125b; miR-128; miR-132; miR-134; miR-138; miR-146; miR-182; miR-183; miR-200b; miR-200c; miR-213; miR-292-5p; miR-297; miR-322; miR-323-3p; miR-325; miR-337; miR-339; miR-345; miR-350; miR-351; miR-370; miR-425; miR-429; miR-433-5p; miR-446; miR-467; miR-874 (see Schratt et al., Nature 439:283-289, 2006; Lugli et al., J. Neurochem. 106:650-661, 2008; Bicker and Schratt, J Cell Mol Med. 12:1466-1476, 2008; Smalheiser and Lugli, Neuromolecular Med. 11:133-140, 2009; Rajasethupathy, Neuron, 63:714-716, 2009; Kye, RNA, 13:1224-1234, 2007; Yu, et al., Exp Cell Res. 314:2618-2633, 2008; Cougot et al., J. Neurosci. 28:13793-13804, 2008; Kawahara, Brain Nerve, 60:1437-1444, 2008), and other small RNAs such as BC200 RNA (Brain Cytoplasmic RNA 200-nucleotides; Dahm et al., Seminars in Cell & Dev. Biol. 18: 216-223, 2007; Mus et al., Proc. Natl. Acad. Sci. USA., 104:10679-10684, 2007). Additional small RNAs useful in the methods of the invention can be identified, for example, based on their enrichment in neurons (and in certain regions of the brain depending on a disease) and intracellular localization in axons and/or dendrites and/or spines and/or synapses. If urine samples are selected for conducting diagnostic methods of the invention, preferred small RNAs for detection would be those small RNAs which are not significantly expressed in cells of the urinary system. Similarly, if blood samples (e.g., serum or plasma) are used for conducting diagnostic methods of the invention, preferred small RNAs for detection would be those small RNAs which are not expressed or are present at very low levels in blood cells.

The methods of the instant invention are based on measurement of levels of certain small RNAs in bodily fluids. The use of bodily fluids that can be obtained by non-invasive or minimally invasive techniques (e.g., as opposed to detection in the brain or CSF) allows for a cheap and minimally invasive or noninvasive diagnostic procedure. Preferred bodily fluids for use in the methods of the invention are blood plasma, serum, urine, and saliva. However, any other bodily fluid can also be used.

Examples of useful methods for measuring small RNA level in bodily fluids include hybridization with selective probes (e.g., using Northern blotting, bead-based flow-cytometry, oligonucleotide microchip [microarray], or solution hybridization assays such as Ambion mirVana mirna Detection Kit), polymerase chain reaction (PCR)-based detection (e.g., stem-loop reverse transcription-polymerase chain reaction [RT-PCR], quantitative RT-PCR based array method [qPCR-array]), or direct sequencing by one of the next generation sequencing technologies (e.g., Helicos small RNA sequencing, miRNA BeadArray (Illumina), Roche 454 (FLX-Titanium), and ABI SOLiD). For review of additional applicable techniques see, e.g., Chen et al., BMC Genomics, 2009, 10:407; Kong et al., J Cell Physiol. 2009; 218:22-25.

In some embodiments, small RNAs are purified prior to quantification. Small RNAs (e.g., miRNAs) can be isolated and purified from bodily fluids by various methods, including the use of commercial kits (e.g., miRNeasy kit [Qiagen], MirVana RNA isolation kit [Ambion/ABI], miRACLE [Agilent], High Pure miRNA isolation kit [Roche], and miRNA Purification kit [Norgen Biotek Corp.]), Trizol extraction (see Example 1, below), concentration and purification on anion-exchangers, magnetic beads covered by RNA-binding substances, or adsorption of certain miRNA on complementary oligonucleotides.

In some embodiments, small RNA degradation in bodily fluid samples and/or during small RNA purification is reduced or eliminated. Useful methods for reducing or eliminating small RNA degradation, include, without limitation, adding RNase inhibitors (e.g., RNasin Plus [Promega], SUPERase-In [ABI], etc.), use of guanidine chloride, guanidine isothiocyanate, N-lauroylsarcosine, sodium dodecyl sulphate (SDS), or a combination thereof. Also, when working with urine samples, lower risk of RNA degradation can be achieved when the sample has been held in the bladder for a shorter time (e.g., less than 4 hours). Reducing small RNA degradation in bodily fluid samples is particularly important when sample storage and transportation is required prior to small RNA quantification.

To account for possible losses of a given small RNA during purification, potential RT-PCR inhibition, small RNA contaminants derived from dying or damaged blood or urine cells during sample isolation and treatment, variations in kidney filtration, etc., various methods of experimental data normalization can be employed. For example, the following normalization methods can be used in the present invention:

a) Concentration of a target small RNA can be normalized to one of ubiquitous miRNAs (e.g., miR-16), small nucleolar RNAs (snoRNAs), miRNAs which are not expressed in neurons (e.g., miR-122a, miR-10b, miR-141), U6 small nuclear RNA (U6 RNA), or neuron body miRNAs (e.g., miR-137, miR-181a, miR-491-5p, miR-298, miR-339 [Kye, RNA, 13:1224-1234, 2007], and others).

b) Synthetic small RNA (e.g., miRNA) oligonucleotides can be synthesized and used as controls for losses during purification and RT-PCR inhibition (by adding them to bodily fluid samples before RNA purification).

c) To account for variations in kidney filtration (when working with urine samples), small RNA concentration in urine can be normalized on creatinine and/or albumin level.

Definitions

The term "neuronal cell body" refers to the portion of a nerve cell that contains the nucleus surrounded by the cytoplasm and the plasma membrane but does not incorporate the dendrites or axons.

The term "neurite" as used herein refers to any projection from the cell body of a neuron. This projection can be an axon, a dendrite, or a spine.

The term "axon" refers to a long, slender projection of a neuron that conducts electrical impulses away from the neuron's cell body or soma. Axons are distinguished from dendrites by several features, including shape (dendrites often taper while axons usually maintain a constant radius), length (dendrites are restricted to a small region around the cell body while axons can be much longer), and function (dendrites usually receive signals while axons usually transmit them). Axons and dendrites make contact with other cells (usually other neurons but sometimes muscle or gland cells) at junctions called synapses.

The term "dendrite" refers to a branched projection of a neuron that acts to conduct the electrochemical stimulation received from other neural cells to the cell body of the neuron from which the dendrites project.

The terms "spine" or "dendritic spine" refer to a small membranous protrusion from a neuron's dendrite that typically receives input from a single synapse of an axon. Dendritic spines serve as a storage site for synaptic strength and help transmit electrical signals to the neuronal cell body. Most spines have a bulbous head (the spine head), and a thin neck that connects the head of the spine to the shaft of the dendrite. The dendrites of a single neuron can contain hundreds to thousands of spines. In addition to spines providing an anatomical substrate for memory storage and synaptic transmission, they may also serve to increase the number of possible contacts between neurons.

The term "synapse" refers to specialized junctions, through which neurons signal to each other and to non-neuronal cells such as those in muscles or glands. A typical neuron gives rise to several thousand synapses. Most synapses connect axons to dendrites, but there are also other types of connections, including axon-to-cell-body, axon-to-axon, and dendrite-to-dendrite. In the brain, each neuron forms synapses with many others, and, likewise, each receives synaptic inputs from many others. As a result, the output of a neuron may depend on the input of many others, each of which may have a different degree of influence, depending on the strength of its synapse with that neuron. There are two major types of synapses, chemical synapses and electrical synapses. In electrical synapses, cells approach within about 3.5 nm of each other, rather than the 20 to 40 nm distance that separates cells at chemical synapses. In chemical synapses, the postsynaptic potential is caused by the opening of ion channels by chemical transmitters, while in electrical synapses it is caused by direct electrical coupling between both neurons. Electrical synapses are therefore faster than chemical synapses.

Within the meaning of the present invention, the term "synapse and/or neurite small RNA" refers to small RNA (e.g., miRNA or BC200 RNA) which (i) is "neuron-enriched", i.e., is present in increased amounts (e.g., at least 5-times higher concentrations) in neurons, as compared to cell types that can be a source of significant amounts of small RNA in a bodily fluid being tested and (ii) is present in a synapse and/or neurite (i.e., axon and/or dendrite and/or spine). To be useful in the diagnostic methods of the present invention, such synapse and/or neurite small RNA should be detectable in bodily fluids as a result of its release from neurons (e.g., due to neurite/synapse destruction or neuronal death).

The term "neuronal body small RNA" as used herein refers to small RNA (e.g., miRNA) which (i) is "neuron-enriched", i.e., is present in increased amounts (e.g., at least 5-times higher concentrations) in neurons, as compared to cell types that can be a source of significant amounts of small RNA in a bodily fluid being tested and (ii) is absent from or present in significantly lower concentrations in neurites or synapses than in neuronal cell bodies.

The terms "neuronal pathology" and "pathological changes in neurons" are used herein to refer to metabolic and/or structural changes in neurons associated with neurite and/or synapse dysfunction and/or neurite destruction and/or synapse loss.

The term "associated with" is used to encompass any correlation, co-occurrence and any cause-and-effect relationship.

The term "development of a neuronal pathology" is used herein to refer to any negative change in the extent/severity of a metabolic and/or structural change in individual neurons and/or any increase in the number of neurons affected. The phrase "improvement of a neuronal pathology" and similar terms refer to any positive change in the extent/severity of a metabolic and/or structural change in individual neurons and/or any decrease in the number of neurons affected.

As used herein, the term "small RNA" refers generally to a heterogeneous group of non-coding RNAs with a variety of regulatory functions including chromatin architecture/epigenetic memory, transcription, RNA splicing, RNA editing, mRNA translation, and RNA turnover. The diagnostic methods of the present invention rely on detecting neurite and/or synapse small RNAs, which can be detected in bodily fluids, such as, for example, microRNAs (miRNAs), Brain Cytoplasmic RNAs BC1/BC200, etc. There are other classes of less characterized small RNAs which can be also useful in the methods of the present invention (reviewed in Kim, Mol. Cells, 2005, 19: 1-15).

The terms "microRNA" or "miRNA" as used herein refer to a class of small approximately 22 nt long non-coding mature RNA molecules. They play important roles in the regulation of target genes by binding to complementary regions of messenger transcripts (mRNA) to repress their translation or regulate degradation (Griffiths-Jones Nucleic Acids Research, 2006, 34, Database issue: D140-D144). Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). Examples of neurite and/or synapse miRNAs useful in the methods of the present invention include, without limitation, miR-7, miR-9, miR-9*, miR-25, miR-26a, miR-26b, miR-98, miR-124, miR-125b, miR-128, miR-132, miR-134, miR-138, miR-146, miR-182, miR-183, miR-200b, miR-200c, miR-213, miR-292-5p, miR-297, miR-322, miR-323-3p, miR-325, miR-337, miR-339, miR-345, miR-350, miR-351, miR-370, miR-425, miR-429, miR-433-5p, miR-446, miR-467 and miR-874. Information on most currently known miRNAs can be found in the miRNA database miRBase (available at the world wide web at mirbase.org). See also Burside et al., BMC Genomics 9:185 (2008); Williams et al., BMC Genomics 8:172 (2007); Landgraf et al., Cell 129:1401 (2007).

The term "miRNA array" refers to a multiplex technology used in molecular biology and in medicine. It consists of an arrayed series of multiple (e.g., thousands) microscopic spots of oligonucleotides, each containing a specific sequence (probe) complementary to a particular target miRNA. After probe-target hybridization under high-stringency conditions the resulting hybrids are usually detected and quantified by quantifying fluorophore-, silver-, or chemiluminescence-labeled targets to determine relative abundance of miRNA. In the methods of the present invention, both custom-made and commercially available miRNA arrays can be used. Examples of useful commercially available miRNA arrays (based on various methods of target labeling, hybrid detection and analysis) include arrays produced by Agilent, Illumina, Invitrogen, Febit, and LC Sciences.

The term "next generation sequencing technologies" broadly refers to sequencing methods which generate multiple sequencing reactions in parallel. This allows vastly increased throughput and yield of data. Non-limiting examples of commonly used next generation sequencing platforms include Helicos small RNA sequencing, miRNA BeadArray (Illumina), Roche 454 (FLX-Titanium), and ABI SOLiD.

An "individual" or "subject" or "animal", as used herein, refers to humans, veterinary animals (e.g., cats, dogs, cows, horses, sheep, pigs, etc.) and experimental animal models of neurodegenerative diseases or other neuronal pathologies (see Examples, below). In a preferred embodiment, the subject is a human.

The term "urinary tract" refers to the organs and ducts, which participate in the secretion and elimination of urine from the body.

The term "purified" as used herein refers to material that has been isolated under conditions that reduce or eliminate the presence of unrelated materials, i.e., contaminants, including native materials from which the material is obtained. For example, RNA purification includes elimination of proteins, lipids, salts and other unrelated compounds present in bodily fluids. Besides, for some methods of analysis a purified miRNA is preferably substantially free of other RNA oligonucleotides contained in bodily fluid samples (e.g., rRNA and mRNA fragments, ubiquitous miRNAs, which are expressed at high levels in almost all tissues [e.g., miR-16], etc.). As used herein, the term "substantially free" is used operationally, in the context of analytical testing of the material. Preferably, purified material substantially free of contaminants is at least 50% pure; more preferably, at least 90% pure, and still more preferably at least 99% pure. Purity can be evaluated by chromatography, gel electrophoresis, composition analysis, biological assay, and other methods known in the art.

As used herein, the term "similarly processed" refers to samples (e.g., bodily fluid samples or purified RNAs) which have been obtained using the same protocol.

The term "a control level" as used herein encompasses predetermined standards (e.g., a published value in a reference) as well as levels determined experimentally in similarly processed samples from control subjects (e.g., age-matched healthy subjects, placebo treated patients, etc.).

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D.N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech.

26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nuc. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Comparison of Different Methods Used for miRNA Purification from Serum or Plasma Since most of the commercially available kits for miRNA isolation have been developed for miRNA purification from cells and tissues various kits are compared with in-house modifications to adjust them for miRNA isolation from serum or plasma. Commercial kits include the miRNeasy kit (Qiagen), the MirVana RNA isolation kit (Ambion/ABI), miRACLE (Agilent), High Pure miRNA isolation kit (Roche), and miRNA Purification kit (Norgen Biotek Corp.). Besides, the in-house techniques based on the use of Trizol (Invitrogen) are developed. In some experiments, miRNA is pre-adsorbed on anion-exchangers, such as Q-Sepharose, or on magnetic beads covered with a RNA-binding material (Q-Sepharose (GE Healthcare), PEI-polyethyleneimine, or other). After Trizol deproteinization, RNA is precipitated with isopropyl alcohol or additionally purified on silica columns. In some experiments, purified RNA is treated with RNAse-free DNAse (Qiagen, ABI, Invitrogen or other). miRNA preparations obtained by different methods are compared using RT PCR. The quality of miRNA preparations is also evaluated by measurement of the RT PCR inhibition (see Example 3, below).

miRNA was purified from plasma and serum samples obtained from the same 5 healthy donors. $10^7$ copies of Arabidopsis thaliana miR-159a (ath-miR-159a) were spiked per 1 ml plasma or serum after addition of guanidine-containing solution for evaluation of miRNA yield. Two techniques, one based on MirVana Paris kit (Ambion/ABI), and another based on Trizol (Invitrogen) deproteinization, and subsequent purification on silica columns, were compared. After RNA purification concentrations of spiked miRNA and human endogenous miR-9, miR-16, and miR-134 in final preps were measured by RT-PCR. MirVana Paris kit was more effective in miRNA isolation then the Trizol-based technique and was selected for future experiments. Although all analyzed miRNA were detectable in serum and plasma and both sample types are suitable for miRNA testing, the final PCR Ct values were about 2 cycles lower for plasma, and the latter was used in subsequent experiments. Based on the quantitative measurement of spiked ath-miR-159a, average yield of miRNA isolated from plasma with MirVana kit was 71.4%.

Example 2

Selection of miRNA for Testing

Tested miRNAs were initially selected based on literature data on their enrichment in brain compartments and presence in neurites (i.e., axons and/or dendrites and/or spines) and/or synapses (Hua et al., *BMC Genomics* 2009, 10:214; Liang et al., BMC Genomics. 2007, 8:166; Landgraf et al., Cell. 2007, 129:1401-1414; Lee et al., RNA. 2008, 14:35-42; Schratt et al., Nature. 439:283-289, 2006; Lugli et al., J. Neurochem. 106:650-661, 2008; Bicker and Schratt, J Cell Mol Med., 12:1466-1476, 2008; Smalheiser and Lugli, Neuromolecular Med. 11:133-140, 2009; Rajasethupathy, Neuron. 63:714-716, 2009; Kye, RNA 13:1224-1234, 2007; Yu et al., Exp Cell Res. 314:2618-2633, 2008; Cougot, et al., J. Neurosci. 28:13793-13804, 2008; Kawahara, Brain Nerve. 60:1437-1444, 2008; Schratt G. Rev Neurosci. 2009; 10:842-849) as well as on their involvement in neurite- and synapse-associated processes (The miR-Ontology Data Base: available at the world wide web at ferrolab.dmi.unict.it/miro/). For normalization, in addition to spiked miRNA, ubiquitous miRNA, such as miR-16, and miRNA expressed in numerous tissues but not in brain, such as miR-10b and miR-141, were used.

Example 3

Detection of an Increase in Levels of Synapse and/or Neurite miRNA in Plasma of AD Patients Plasma samples were obtained from patients diagnosed with developed AD by cognitive test and brain imaging. Profiles of several neuron-enriched miRNAs from plasma of these patients were analyzed using RT-PCR with primers and probes for each individual miRNA (ABI). The amount of RNA equivalent to 30 μL plasma were taken in each PCR reaction, and ⅟₁₅ of RT product was taken into final PCR. Thus, the amount of miRNA equivalent to 2 μL plasma was detected. The results were normalized per various miRNA, usually per ubiquitous miR-16, converted into Relative Quantity (RQ) of miRNA according the ABI protocol ($2^{-\Delta ct}$), and compared with miRNA profiles from age-matched controls. In addition, data obtained with neurite and/or synapse miRNA were compared with data obtained with neuronal body miRNA.

As shown in FIGS. 1A-G, the data obtained clearly demonstrate that concentrations of many neuron-enriched miRNAs increase in plasma of AD patients. However, this effect is much more prominent for neurite and/or synapse miRNAs (miR-7 (A), miR-125b (B), miR-128 (C), miR-132 (D), and miR-323-3p (E)) than for neuronal body miRNAs (miR-181a (F) and miR-491-5p (G)).

Other techniques can be used for measuring miRNA concentration in bodily fluids with some precautions. For example, application of next generation sequencing technologies to quantitative analysis of miRNAs and other small RNAs in bodily fluids is complicated by two factors. First, fragments of ribosomal RNA (rRNA) and to a lesser degree messenger RNA (mRNA) comprise major part of small oligonucleotides present in bodily fluids, which complicates sequencing of miRNAs and some of the other small RNAs, which are present in a much smaller number of copies. Second, some ubiquitous miRNAs, which are expressed at high levels in almost all tissues (e.g., miR-16), can be present in bodily fluids in the million times larger number of copies than miRNAs of interest. To overcome these problems, prior to performing quantitative sequencing of relatively rare neurite and/or synapse miRNAs and other neurite and/or synapse small RNAs, the preparations of RNA from bodily fluids can be depleted from rRNA fragments using, for example, Selective Hybridization and Removal of rRNA kit (Invitrogen), and other oligonucleotides present in a huge number of copies can be removed by hybridization with respective complementary DNA sequences. These depleted RNA preparations can be then analyzed using one of new generation sequencing techniques, such as, e.g., Helicos small RNA sequencing or the miRNA BeadArray (Illumina) miRNAs and/or other small RNAs, which provide the most reproducible and reliable results (i.e., change in level characteristic of a certain neurodegenerative disease), can be selected as potential biomarkers and analyzed by RT-PCR or other methods.

Example 4

Demonstration that the Increase in Levels of Neurite and/or Synapse miRNAs in MCI Patients is More Significant and Precedes the Increase in Levels of Neuronal Body miRNAs Plasma samples were obtained from patients diagnosed with MCI. Profiles of neuron-enriched miRNAs from plasma of these patients were analyzed using RT-PCR with primers and probes for each individual miRNA (ABI). The amount of RNA equivalent to 30 μL plasma were taken in each PCR reaction, and ⅟15 of RT product was taken into final PCR. Thus, the amount of miRNA equivalent to 2 μL plasma was detected. The results were normalized per various miRNA, converted into Relative Quantity (RQ) of miRNA according the ABI protocol ($2^{-\Delta ct}$), and compared with miRNA profiles from age-matched controls.

When normalization per spiked non-human miRNA was performed, which gives relative miRNA concentration per 1 ml plasma, some plasma samples from MCI patients contained more neurite and/or synapse miRNAs (FIG. 2, miR-7 (A) and miR-874 (B)).

At the same time concentrations of neuronal body miRNAs were not changed in the plasma of MCI patients (FIG. 2, miR-181a (C) and miR-491-5p (D)).

Figure 3A:
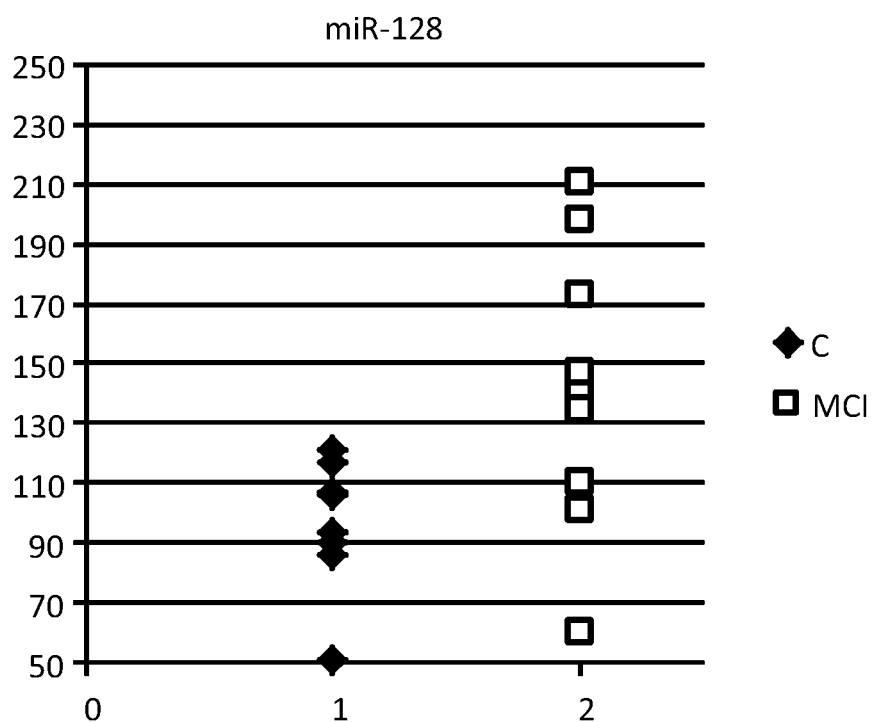
FIGS. 3A-B are graphs showing comparison of miRNA concentrations in plasma of MCI patients and age-matched controls. All concentrations were normalized per miR-141 and presented in relative units (ordinate axis). miR-128 (A) is neurite and synapse miRNA; miR-539 (B) is neuronal body miRNA.
Figure 3B:
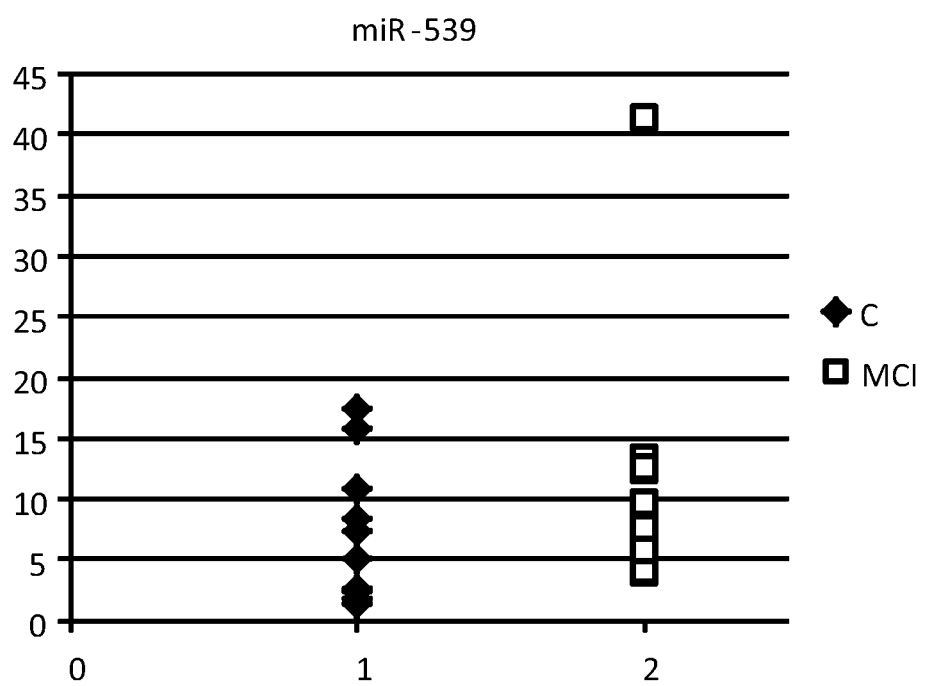
Figure 4A:
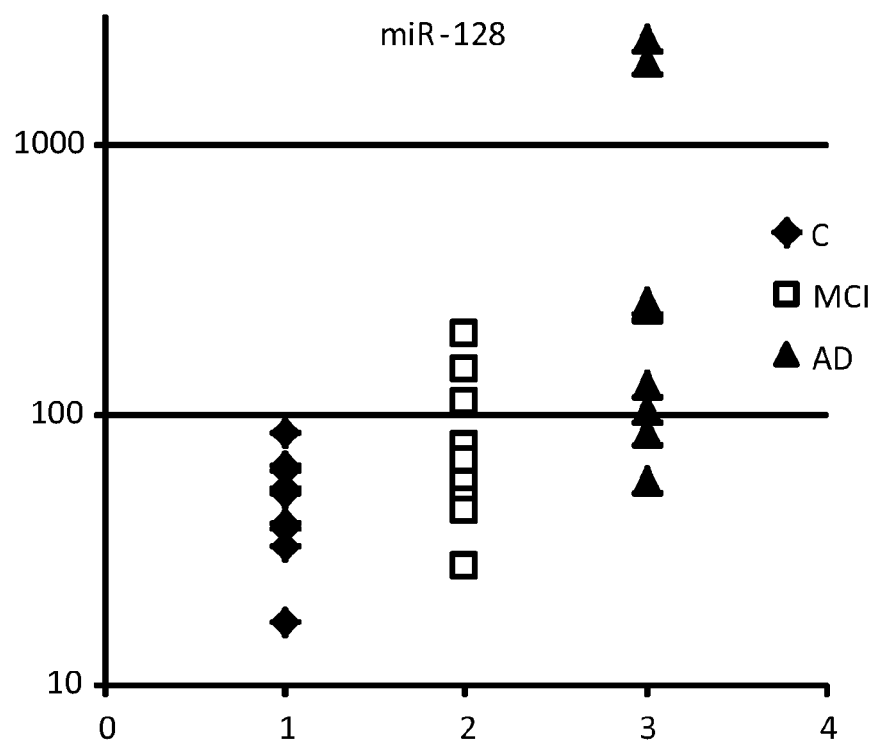
FIGS. 4A-D are graphs showing comparison of miRNA concentrations in plasma of MCI and AD patients and age-matched controls. Concentrations of neurite and/or synapse miRNA miR-128 (A), miR-132 (B), miR-370 (C), and miR-125b (D) were normalized per miR-181a (neuronal body miRNA) and presented in relative units (ordinate axis).
Figure 4B:
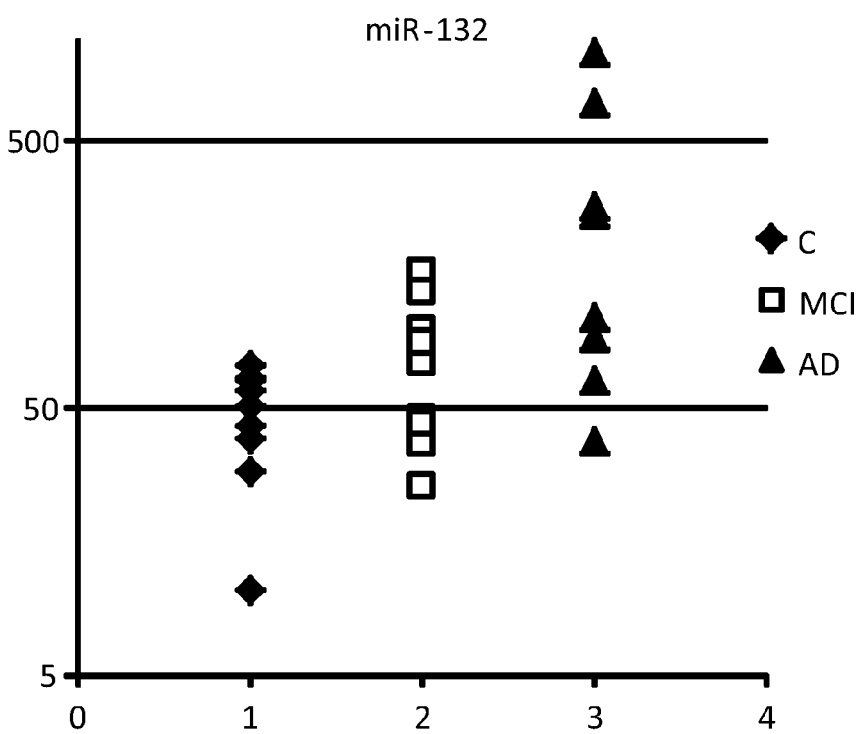
Figure 4C:
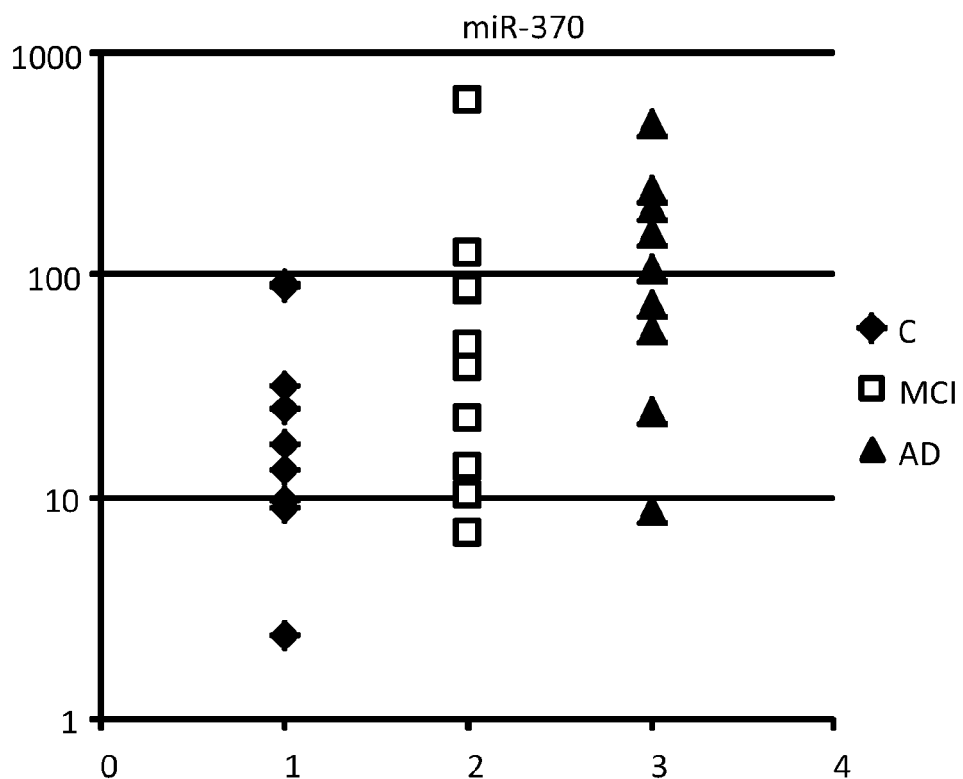
Figure 4D:
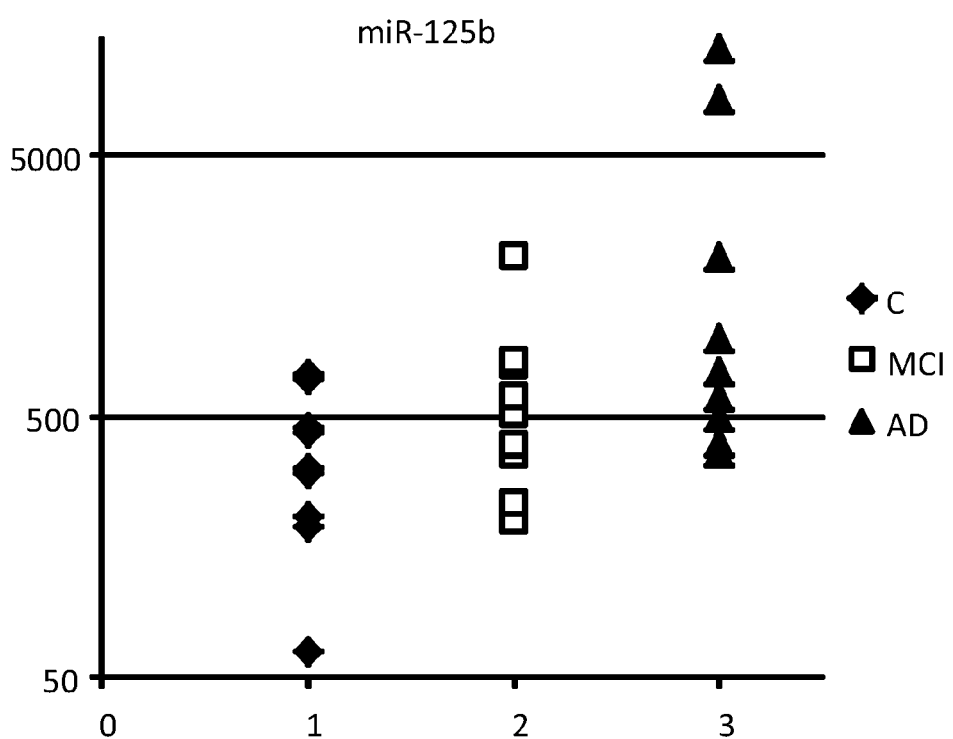

Similar results were obtained, when miRNA concentrations in plasma were normalized per miR-141, which is expressed in many organs but not in the brain (FIGS. 3A-B).

Example 5

Comparison of Neuron-Enriched miRNA Levels in Plasma of Control, MCI and AD Patients Since concentrations of neurite and/or synapse miRNAs increase and concentrations of neuronal body miRNAs are practically unchanged in plasma of MCI patients, their ratios were used for analysis of disease development. Plasma samples were obtained from patients diagnosed with MCI and AD. Profiles of neuron-enriched miRNA from plasma of these patients were analyzed using RT-PCR with primers and probes for each individual miRNA (ABI). The amount of RNA equivalent to 30 μL plasma were taken in each PCR reaction, and ⅟15 of RT product was taken into final PCR. Thus, the amount of miRNA equivalent to 2 μL plasma was detected. Then the concentrations of neurite and/or synapse miRNAs were normalized per miRNA, located mainly in neuronal body, according the ABI protocol ($2^{-\Delta ct}$), and compared with respective numbers from age-matched controls.

As shown in FIGS. 4A-D, the data obtained demonstrate a clear trend of increasing concentrations of some neurite and/or synapse miRNAs (i.e., miR-128 (A), miR-132 (B), miR-370 (C), and miR-125b (D)) from Control to MCI to AD. These data suggest that periodic screening of elderly people can help with early diagnostics and monitoring of MCI and AD.

Example 6

Detection of Neurite Destruction and Synapse Loss (in the Absence of Massive Neuronal Cell Death) in Animal Models of Early and Mild AD by Analysis of Neurite and/or Synapse miRNAS in Blood The following animal models of AD can be used to detect neurite destruction and/or synapse loss (in the absence of massive neuronal cell death) using the analysis of neurite and/or synapse miRNAs in bodily fluids. The same animal models are useful for testing the sensitivity and adjusting the conditions of the diagnostic and monitoring methods of the present invention and for identifying additional neurite and/or synapse miRNAs and other small RNA molecules that can be used as markers of neurodegenerative diseases.

Various transgenic mice models are currently available that overexpress Familial Alzheimer's disease (FAD) mutant forms of human APP. Most currently studied models show cognitive deficits and age-related disruption of synaptic markers and amyloid plaque deposition, but few strains show evidence of significant cell death (Janus et al. 2000; Ashe 2001; Chapman et al. 2001; Richardson & Burns 2002). Examples of such transgenic mice are (i) PDAPP mice overexpressing hAPP V717F, (ii) Tg2576 mice overexpressing hAPP 695 mutated with both K670N and M671L (Hsiao et al., 1996), (iii) TgAPP/Ld/2 mice overexpressing hAPP V6421; (iv) mice overexpressing hAPP V717I; (v) human APP transgenic mice with mutation of Asp-664, which prevents caspase cleavage and accumulation of cytotoxic peptide APP-C31 with partial reversal of Alzheimer's-like pathology (Galvan et al. Proc Natl Acad Sci USA. 2006; 103:7130-7135). Also useful is a double mutant transgenic mouse model expressing APP minigenes that encode FAD-linked APP mutants and an early-onset familial AD (FAD)-linked human presenilin 1 (PS1) variant (A246E) and a chimeric mouse/human APP harboring mutations linked to Swedish FAD kindreds (APPswe) (see U.S. Pat. No. 5,912,410; Borchelt et al., Neuron 1997, 19:939-945; Holcomb et al., 1998). These mice develop numerous amyloid deposits much earlier than age-matched mice expressing APPswe and wild-type human PS1. Expression of APP minigenes that encode FAD-linked APP mutants and, in particular, co-expression of the mutant human PS1 A246E and APPswe elevates levels of Aβ in the brain, and these mice develop numerous diffuse Aβ deposits and plaques in the hippocampus and cortex (Calhoun et al., Proc. Natl. Acad. Sci. USA 1999; 96:14088-14093). Similarly to humans suffering from AD, these and other transgenic animal models are characterized by various cognitive defects such as loss of neurons, learning deficits, problems in object recognition memory, and problems with alternation-spatial reference and working memory (Chen et al., Nature 2000; 408:975-979).

To detect neurite destruction and synapse loss (in the absence of massive neuronal cell death), neurite and/or synapse miRNAs are isolated from the blood serum/plasma of AD model transgenic mice and analyzed by RT-PCR, and data obtained are compared with brain histopathology.

* * *

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for detecting in a subject neurite destruction and synapse loss, associated with a neuronal pathology, prior to neuronal cell death, which method comprises:
   a. measuring the level of a synapse or neurite small RNA in a bodily fluid sample collected from the subject, wherein the bodily fluid is selected from the group consisting of blood plasma, serum, urine, and saliva;
   b. measuring the level of a normalizer small RNA in the same bodily fluid sample collected from the subject, wherein the normalizer small RNA is a neuronal body small RNA or a small RNA which is not expressed in brain or miRNA selected from the group consisting of miR-181a, miR-491-5p, miR-10b and miR-141;
   c. calculating the ratio of the levels of the small RNAs measured in steps (a) and (b);
   d. comparing the ratio of the levels of the small RNAs calculated in step (c) with a corresponding control ratio, wherein the control ratio is selected from the group consisting of (i) a predetermined standard, (ii) the ratio of said synapse or neurite small RNA to said normalizer small RNA in a similarly processed bodily fluid sample from the same subject collected in the past, and (iii) the ratio of said synapse or neurite small RNA to said normalizer small RNA in a similarly processed bodily fluid sample from a control subject, and
   e. (i) identifying the subject as being afflicted with neurite destruction and synapse loss associated with the neuronal pathology when the ratio of the levels of the small RNAs calculated in step (c) is higher than the corresponding control ratio or (ii) identifying the subject as not being afflicted with neurite destruction and synapse loss associated with the neuronal pathology when the ratio of the levels of the small RNAs calculated in step (c) is not higher than the corresponding control ratio.

2. The method of claim 1, wherein the neuronal pathology is associated with a neurodegenerative disease.

3. The method of claim 1, wherein the synapse or neurite small RNA is miRNA selected from the group consisting of miR-7, miR-9, miR-9*, miR-25, miR-26a, miR-26b, miR-98, miR-124, miR-125b, miR-128, miR-132, miR-134, miR-138, miR-146, miR-182, miR-183, miR-200b, miR-200c, miR-213, miR-292-5p, miR-297, miR-322, miR-323-3p, miR-325, miR-337, miR-339, miR-345, miR-350, miR-351, miR-370, miR-425, miR-429, miR-433-5p, miR-446, miR-467, and miR-874.

4. The method of claim 1, comprising measuring the level of two or more synapse or neurite small RNAs.

5. A method for monitoring changes in neurite destruction and synapse loss associated with development of a neuronal pathology in a subject, which method comprises:
   a. measuring the level of a synapse or neurite small RNA in two or more bodily fluid samples collected from the subject, wherein the samples have been collected at spaced apart time points, and wherein the bodily fluid is selected from the group consisting of blood plasma, serum, urine, and saliva;
   b. measuring the level of a normalizer small RNA in the same bodily fluid samples as in step (a), wherein the normalizer small RNA is a neuronal body small RNA or a small RNA which is not expressed in brain or miRNA selected from the group consisting of miR-181a, miR-491-5p, miR-10b and miR-141;
   c. calculating the ratio of the levels of the small RNAs measured in steps (a) and (b) for each bodily fluid sample;
   d. comparing the ratios of the levels of the small RNAs calculated in step (c) between the earlier collected and later collected bodily fluid sample(s), and
   e. (i) determining that the neurite destruction and synapse loss associated with the neuronal pathology in the subject is increased if the ratio of the levels of the small RNAs calculated in step (c) is increased in the later collected bodily fluid sample(s) as compared to the earlier collected sample(s); (ii) determining that the neurite destruction and synapse loss associated with the neuronal pathology in the subject continues at the same rate if the ratio of the levels of the small RNAs calculated in step (c) is not changed in the later collected bodily fluid sample(s) as compared to the earlier collected sample(s), and (iii) determining that the neurite destruction and synapse loss associated with the neuronal pathology in the subject is decreased if the ratio of the levels of the small RNAs calculated in step (c) is decreased in the later collected bodily fluid sample(s) as compared to the earlier collected sample(s).

6. The method of claim 5, wherein the neuronal pathology is associated with a neurodegenerative disease.

7. The method of claim 5, wherein the synapse or neurite small RNA is miRNA selected from the group consisting of miR-7, miR-9, miR-9*, miR-25, miR-26a, miR-26b, miR-98, miR-124, miR-125b, miR-128, miR-132, miR-134, miR-138, miR-146, miR-182, miR-183, miR-200b, miR-200c, miR-213, miR-292-5p, miR-297, miR-322, miR-323-3p, miR-325, miR-337, miR-339, miR-345, miR-350, miR-351, miR-370, miR-425, miR-429, miR-433-5p, miR-446, miR-467, and miR-874.

8. The method of claim 5, comprising measuring the level of two or more synapse or neurite small RNAs.

9. A method for monitoring the effect of a treatment on neurite destruction and synapse loss in a subject suffering from a neuronal pathology, which method comprises:
   a. measuring the level of a synapse or neurite small RNA in a bodily fluid sample collected from the subject prior to initiation of the treatment, wherein the bodily fluid is selected from the group consisting of blood serum, blood plasma, urine, and saliva;
   b. measuring the level of a normalizer small RNA in the same bodily fluid sample as in step (a), wherein the normalizer small RNA is a neuronal body small RNA or a small RNA which is not expressed in brain or miRNA selected from the group consisting of miR-181a, miR-491-5p, miR-10b and miR-141;

c. calculating the ratio of the levels of the small RNAs measured in steps (a) and (b);
d. measuring the level of the same synapse or neurite small RNAs) as in step (a) in one or more bodily fluid sample(s) collected from the subject in the course of or following the treatment, wherein the bodily fluid is selected from the group consisting of blood plasma, serum, urine, and saliva;
e. measuring the level of the same normalizer small RNA as in step (b) in the same bodily fluid sample(s) as in step (d);
f. calculating the ratio of the levels of the small RNAs measured in steps (d) and (e) for each bodily fluid sample;
g. comparing the ratios of the levels of the small RNAs calculated in steps (c) and (f), and optionally comparing the ratios of the levels of the small RNAs calculated in step (f) between different samples in step (d), and
h. (i) determining that the treatment is effective in decreasing neurite destruction and synapse loss if the ratio of the levels of the small RNAs calculated in step (c) is higher than the corresponding ratio(s) calculated in step (f) or (ii) determining that the treatment is not effective in decreasing neurite destruction and synapse loss if the ratio of the levels of the small RNAs calculated in step (c) is not higher than the corresponding ratio(s) calculated in step (f).

10. The method of claim 9, wherein the neuronal pathology is associated with a neurodegenerative disease.

11. The method of claim 9, wherein the synapse or neurite small RNA is miRNA selected from the group consisting of miR-7, miR-9, miR-9*, miR-25, miR-26a, miR-26b, miR-98, miR-124, miR-125b, miR-128, miR-132, miR-134, miR-138, miR-146, miR-182, miR-183, miR-200b, miR-200c, miR-213, miR-292-5p, miR-297, miR-322, miR-323-3p, miR-325, miR-337, miR-339, miR-345, miR-350, miR-351, miR-370, miR-425, miR-429, miR-433-5p, miR-446, miR-467, and miR-874.

12. The method of claim 9, comprising measuring the level of two or more synapse or neurite small RNAs.

* * * * *

UNITED STATES PATENT AND TRADEMARK OFFICE
CERTIFICATE OF CORRECTION

| | | |
|---|---|---|
| PATENT NO. | : 8,648,017 B2 | Page 1 of 1 |
| APPLICATION NO. | : 13/508262 | |
| DATED | : February 11, 2014 | |
| INVENTOR(S) | : Samuil R. Umansky and Kira S. Sheinerman | |

It is certified that error appears in the above-identified patent and that said Letters Patent is hereby corrected as shown below:

In the Claims:

Column 20, line 8, in Claim 5, after "subject," insert --wherein neurite destruction and synapse loss, associated with the neuronal pathology, is detected in an initial sample from the subject prior to neuronal cell death and,--

Column 20, line 57, in Claim 9, before "measuring" insert --detecting neurite destruction and synapse loss associated with the neuronal pathology in the subject, prior to neuronal cell death, by--

Column 21, line 4, in Claim 9, delete "RNAs)" and insert --RNA--

Signed and Sealed this
Twenty-ninth Day of April, 2014

Michelle K. Lee
*Deputy Director of the United States Patent and Trademark Office*